US009609934B2

(12) United States Patent
Thevenet

(10) Patent No.: US 9,609,934 B2
(45) Date of Patent: *Apr. 4, 2017

(54) METHOD OF APPLYING MAKEUP BY MEANS OF A MAGNETIC COMPOSITION INCLUDING AT LEAST ONE INTERFERENTIAL PIGMENT

(75) Inventor: Ludovic Thevenet, Bourg la Reine (FR)

(73) Assignee: L'OREAL, Paris (FR)

( * ) Notice: Subject to any disclaimer, the term of this patent is extended or adjusted under 35 U.S.C. 154(b) by 1930 days.

This patent is subject to a terminal disclaimer.

(21) Appl. No.: 11/663,772

(22) PCT Filed: Jul. 8, 2005

(86) PCT No.: PCT/FR2005/050565
§ 371 (c)(1),
(2), (4) Date: Aug. 16, 2007

(87) PCT Pub. No.: WO2006/037907
PCT Pub. Date: Apr. 13, 2006

(65) Prior Publication Data
US 2008/0105272 A1    May 8, 2008

Related U.S. Application Data

(60) Provisional application No. 60/619,928, filed on Oct. 20, 2004.

(30) Foreign Application Priority Data

Oct. 5, 2004 (FR) ...................... 04 10501

(51) Int. Cl.
| A45D 34/00 | (2006.01) |
| A45D 33/00 | (2006.01) |
| A61K 8/19  | (2006.01) |
| A61Q 1/00  | (2006.01) |
| A61Q 1/02  | (2006.01) |
| A61Q 1/06  | (2006.01) |
| A61Q 3/02  | (2006.01) |
| A45D 29/00 | (2006.01) |

(52) U.S. Cl.
CPC ............ *A45D 34/00* (2013.01); *A45D 33/00* (2013.01); *A61K 8/19* (2013.01); *A61Q 1/00* (2013.01); *A61Q 1/02* (2013.01); *A61Q 1/06* (2013.01); *A61Q 3/02* (2013.01); *A45D 29/004* (2013.01); *A61K 2800/42* (2013.01); *A61K 2800/47* (2013.01); *A61K 2800/88* (2013.01)

(58) Field of Classification Search
None
See application file for complete search history.

(56) References Cited

U.S. PATENT DOCUMENTS

| 3,030,967 A |   | 4/1962  | Peyron |
| 3,461,885 A |   | 8/1969  | Coveney |
| 3,516,422 A |   | 6/1970  | Bechtold et al. |
| 3,623,732 A |   | 11/1971 | Peeples |
| 3,791,386 A |   | 2/1974  | McDonald |
| 3,791,864 A |   | 2/1974  | Steingroever |
| 3,836,537 A |   | 9/1974  | Boerwinkle et al. |
| 3,910,862 A |   | 10/1975 | Barabas et al. |
| 3,926,659 A | * | 12/1975 | Bernhard et al. ............. 106/418 |
| 3,937,811 A |   | 2/1976  | Papantoniou et al. |
| 4,031,307 A |   | 6/1977  | DeMartino et al. |
| 4,055,377 A | * | 10/1977 | Erickson et al. ............. 359/518 |
| 4,131,576 A |   | 12/1978 | Iovine et al. |
| 4,223,009 A |   | 9/1980  | Chakrabarti |
| 4,318,844 A |   | 3/1982  | Kohler et al. |
| 4,425,326 A |   | 1/1984  | Guillon et al. |
| 4,470,715 A |   | 9/1984  | Reuchlin et al. |
| 4,614,366 A |   | 9/1986  | North et al. |
| 4,693,935 A |   | 9/1987  | Mazurek |
| 4,728,571 A |   | 3/1988  | Clemens et al. |
| 4,972,037 A |   | 11/1990 | Garbe et al. |

(Continued)

FOREIGN PATENT DOCUMENTS

| DE | 196 45 648     | 7/1997  |
| DE | 102 19 196 A1  | 11/2003 |
| DE | 102 19 296     | 11/2003 |
| EP | 0 096 459 A2   | 12/1983 |
| EP | 0 113 920 A2   | 7/1984  |
| EP | 0 080 976 B1   | 9/1986  |
| EP | 0 388 582 A2   | 9/1990  |
| EP | 0 412 704 A2   | 2/1991  |
| EP | 0 412 707 A1   | 2/1991  |
| EP | 0 416 747 A1   | 3/1991  |

(Continued)

OTHER PUBLICATIONS

Berns, Roy S.; "Billmeyer and Saltzman's Principles of Color Technology," 3rd edition 2000, John Wiley & Sons; pp. 12, 13, 138 and 139.*

(Continued)

*Primary Examiner* — David J Blanchard
*Assistant Examiner* — Ivan Greene
(74) *Attorney, Agent, or Firm* — Oliff PLC

(57) ABSTRACT

The present invention relates to a method of applying makeup to keratinous substances, in particular the skin, the lips, the nails, or hair, the method comprising the following steps:
  depositing at least one cosmetic composition on the surface to be made up, the cosmetic composition comprising:
    bodies that present non-zero magnetic susceptibility and that are movable under the effect of a magnetic field; and
    at least one interferential pigment; and
  exposing at least part of the composition to a magnetic field, so as to modify the orientation and/or displace at least some of the magnetic bodies.

26 Claims, 3 Drawing Sheets

(56) References Cited

U.S. PATENT DOCUMENTS

| | | |
|---|---|---|
| 4,981,902 A | 1/1991 | Mitra et al. |
| 4,981,903 A | 1/1991 | Garbe et al. |
| 5,030,669 A | 7/1991 | Hendrickson et al. |
| 5,040,914 A | 8/1991 | Fitjer |
| 5,061,481 A | 10/1991 | Suzuki et al. |
| 5,066,485 A | 11/1991 | Brieva et al. |
| 5,122,418 A | 6/1992 | Nakane et al. |
| 5,127,952 A | 7/1992 | Persello et al. |
| 5,133,805 A * | 7/1992 | Kurata et al. .................. 106/456 |
| 5,162,410 A | 11/1992 | Sweet |
| 5,188,815 A | 2/1993 | Coates et al. |
| 5,188,899 A | 2/1993 | Matsumoto et al. |
| 5,199,808 A | 4/1993 | Gueret |
| 5,206,011 A | 4/1993 | Pappas et al. |
| 5,209,924 A | 5/1993 | Garbe et al. |
| 5,219,560 A | 6/1993 | Suzuki et al. |
| 5,291,345 A | 3/1994 | Umeda et al. |
| 5,307,847 A | 5/1994 | Pavenick et al. |
| 5,316,026 A * | 5/1994 | Jenkins .......................... 132/285 |
| 5,330,747 A | 7/1994 | Krzysik |
| 5,356,617 A | 10/1994 | Schlossman |
| 5,362,485 A | 11/1994 | Hayama et al. |
| 5,380,359 A | 1/1995 | Honda et al. |
| 5,393,526 A | 2/1995 | Castro |
| 5,424,006 A | 6/1995 | Murayama et al. |
| 5,451,610 A | 9/1995 | Krzysik |
| 5,468,477 A | 11/1995 | Kumar et al. |
| 5,472,798 A | 12/1995 | Kumazawa et al. |
| 5,486,354 A | 1/1996 | Defossez et al. |
| 5,512,273 A | 4/1996 | Martin |
| 5,562,706 A * | 10/1996 | Lauterbach et al. .............. 607/3 |
| 5,625,005 A | 4/1997 | Mallya et al. |
| 5,641,835 A | 6/1997 | Smith et al. |
| 5,643,672 A | 7/1997 | Marchi et al. |
| 5,658,574 A | 8/1997 | Bahary et al. |
| 5,683,706 A | 11/1997 | LaFleur et al. |
| 5,705,093 A | 1/1998 | Coates et al. |
| 5,725,483 A | 3/1998 | Podolsky |
| 5,725,882 A | 3/1998 | Kumar et al. |
| 5,846,310 A | 12/1998 | Noguchi et al. |
| 5,849,275 A | 12/1998 | Calello et al. |
| 5,849,318 A | 12/1998 | Imai et al. |
| 5,851,517 A | 12/1998 | Mougin et al. |
| 5,856,653 A | 1/1999 | Boudreaux |
| 5,873,375 A * | 2/1999 | Johnson et al. .............. 132/200 |
| 5,874,069 A | 2/1999 | Mendolia et al. |
| 5,913,631 A | 6/1999 | Landry |
| 5,919,441 A | 7/1999 | Mendolia et al. |
| 5,931,166 A | 8/1999 | Weber et al. |
| 5,948,393 A | 9/1999 | Tomomasa et al. |
| 5,954,871 A | 9/1999 | Nicolas-Morgantini et al. |
| 5,981,680 A | 11/1999 | Petroff et al. |
| 6,001,338 A | 12/1999 | Mondet |
| 6,033,648 A | 3/2000 | Candau |
| 6,033,650 A | 3/2000 | Calello et al. |
| 6,033,655 A | 3/2000 | Lahanas et al. |
| 6,051,216 A | 4/2000 | Barr et al. |
| 6,071,632 A | 6/2000 | Hall-Goulle |
| 6,074,654 A | 6/2000 | Drechsler et al. |
| 6,117,435 A | 9/2000 | Painter et al. |
| 6,117,574 A | 9/2000 | Watanabe et al. |
| 6,136,907 A | 10/2000 | Sunamori et al. |
| 6,177,093 B1 | 1/2001 | Lombardi et al. |
| 6,203,781 B1 | 3/2001 | Chevalier et al. |
| 6,203,909 B1 | 3/2001 | Chassot |
| 6,209,548 B1 * | 4/2001 | Harrison et al. .............. 132/74.5 |
| 6,254,876 B1 | 7/2001 | de la Poterie et al. |
| 6,280,655 B1 | 8/2001 | Xu et al. |
| 6,299,979 B1 | 10/2001 | Neubauer et al. |
| 6,358,495 B1 | 3/2002 | Nishihama et al. |
| 6,387,498 B1 | 5/2002 | Coulter et al. |
| 6,403,106 B1 | 6/2002 | Sebag et al. |
| 6,428,773 B1 | 8/2002 | Oko et al. |
| 6,432,386 B1 | 8/2002 | Rollat-Corvol et al. |
| 6,432,423 B1 | 8/2002 | Maignan et al. |
| 6,451,294 B1 | 9/2002 | Simon |
| 6,477,398 B1 * | 11/2002 | Mills ........................... 600/409 |
| 6,488,945 B2 * | 12/2002 | Sato ............................ 424/401 |
| 6,491,927 B1 | 12/2002 | Arnaud et al. |
| 6,503,761 B1 | 1/2003 | Koenig et al. |
| 6,515,717 B1 | 2/2003 | Jiang et al. |
| 6,517,628 B1 | 2/2003 | Pfaff et al. |
| 6,517,818 B1 | 2/2003 | Golz-Berner et al. |
| 6,545,809 B1 | 4/2003 | Phillips |
| 6,582,684 B1 | 6/2003 | Abrahamson |
| 6,589,331 B2 * | 7/2003 | Ostertag et al. .............. 106/460 |
| 6,645,286 B2 | 11/2003 | Ostertag et al. |
| 6,686,397 B2 | 2/2004 | Jaehne et al. |
| 6,753,002 B2 | 6/2004 | George et al. |
| 6,846,474 B2 | 1/2005 | Nayfeh et al. |
| 6,884,289 B2 | 4/2005 | Schoen et al. |
| 7,056,498 B2 | 6/2006 | Chevalier et al. |
| 7,060,371 B2 | 6/2006 | Akiyama et al. |
| 7,258,900 B2 | 8/2007 | Raksha et al. |
| 7,270,770 B2 | 9/2007 | Sage et al. |
| 7,306,809 B2 | 12/2007 | Sojka et al. |
| 7,329,287 B2 | 2/2008 | Simonet et al. |
| 7,329,719 B2 | 2/2008 | Pavlin |
| 2001/0022025 A1 | 9/2001 | Skipper |
| 2001/0033766 A1 | 10/2001 | Gueret |
| 2002/0012683 A1 | 1/2002 | Henrion et al. |
| 2002/0015965 A1 | 2/2002 | Sweeting |
| 2002/0031870 A1 | 3/2002 | Bryant |
| 2002/0039562 A1 | 4/2002 | Kobayashi et al. |
| 2002/0041853 A1 | 4/2002 | Ishii et al. |
| 2002/0064509 A1 | 5/2002 | Grimm et al. |
| 2002/0070121 A1 | 6/2002 | Nayfeh et al. |
| 2002/0117084 A1 | 8/2002 | Hayashi et al. |
| 2002/0134282 A1 | 9/2002 | Ostertag et al. |
| 2002/0164192 A1 | 11/2002 | Gueret |
| 2002/0169244 A1 * | 11/2002 | Ostertag et al. .............. 524/440 |
| 2002/0182383 A1 * | 12/2002 | Phillips et al. ............... 428/199 |
| 2002/0182409 A1 * | 12/2002 | Gueret .......................... 428/364 |
| 2002/0192448 A1 | 12/2002 | Schoen et al. |
| 2003/0007942 A1 | 1/2003 | Koenig |
| 2003/0012752 A1 | 1/2003 | Sara |
| 2003/0031870 A1 | 2/2003 | Argoitia et al. |
| 2003/0039621 A1 | 2/2003 | Arnaud et al. |
| 2003/0064039 A1 | 4/2003 | Kolodziej et al. |
| 2003/0064086 A1 | 4/2003 | Carrion et al. |
| 2003/0072602 A1 | 4/2003 | Gueret |
| 2003/0082121 A1 * | 5/2003 | Borsakian et al. ............. 424/61 |
| 2003/0118531 A1 | 6/2003 | Kolodziej et al. |
| 2003/0130323 A1 | 7/2003 | Jaehne et al. |
| 2003/0134761 A1 | 7/2003 | Sebillotte-Arnaud et al. |
| 2003/0180232 A1 | 9/2003 | Ishii et al. |
| 2003/0180535 A1 | 9/2003 | Horino et al. |
| 2003/0228339 A1 | 12/2003 | El-Nokaly et al. |
| 2004/0001869 A1 | 1/2004 | Yago et al. |
| 2004/0009309 A1 * | 1/2004 | Raksha et al. ................ 427/598 |
| 2004/0012683 A1 | 1/2004 | Yamasaki et al. |
| 2004/0105827 A1 | 6/2004 | Grimm et al. |
| 2004/0109837 A1 | 6/2004 | Mellul et al. |
| 2004/0175338 A1 | 9/2004 | Filippi et al. |
| 2004/0228818 A1 | 11/2004 | Simon et al. |
| 2004/0228890 A1 | 11/2004 | Blin et al. |
| 2004/0241118 A1 | 12/2004 | Simon et al. |
| 2005/0025728 A1 | 2/2005 | De Rigal et al. |
| 2005/0036964 A1 | 2/2005 | Camus et al. |
| 2005/0118122 A1 | 6/2005 | Simon et al. |
| 2005/0191337 A1 | 9/2005 | Gueret |
| 2005/0238979 A1 | 10/2005 | Dumousseaux |
| 2005/0249540 A1 | 11/2005 | Gueret |
| 2005/0257335 A1 | 11/2005 | Dumousseaux |
| 2005/0257715 A1 | 11/2005 | Dumousseaux |
| 2005/0260146 A1 | 11/2005 | Blin |
| 2005/0276767 A1 | 12/2005 | Blin et al. |
| 2006/0018854 A1 | 1/2006 | Dumousseaux et al. |
| 2006/0039876 A1 | 2/2006 | Dumousseaux et al. |
| 2006/0041054 A1 | 2/2006 | Dumousseaux et al. |
| 2006/0051382 A1 | 3/2006 | Vidal |
| 2006/0088484 A1 | 4/2006 | Thevenet |
| 2006/0099160 A1 | 5/2006 | Dumousseaux |
| 2006/0118663 A1 | 6/2006 | Herzing |

(56) References Cited

U.S. PATENT DOCUMENTS

| | | | |
|---|---|---|---|
| 2006/0134044 A1* | 6/2006 | Blin et al. | 424/70.11 |
| 2006/0165621 A1 | 7/2006 | Dubertret et al. | |
| 2006/0280705 A1 | 12/2006 | Bruechert et al. | |
| 2006/0280764 A1 | 12/2006 | Watanabe et al. | |
| 2007/0009454 A1 | 1/2007 | Thevenet | |
| 2007/0231940 A1 | 10/2007 | Gourlaouen et al. | |
| 2008/0014158 A1 | 1/2008 | Lion et al. | |
| 2008/0044443 A1 | 2/2008 | Thevenet | |
| 2008/0050324 A1 | 2/2008 | Thevenet | |
| 2008/0105272 A1 | 5/2008 | Thevenet | |
| 2008/0124288 A1 | 5/2008 | Thevenet | |
| 2008/0127990 A1 | 6/2008 | Thevenet | |
| 2009/0130037 A1 | 5/2009 | Thevenet et al. | |

FOREIGN PATENT DOCUMENTS

| | | |
|---|---|---|
| EP | 0 581 651 | 2/1994 |
| EP | 0 582 152 A2 | 2/1994 |
| EP | 0 587 908 | 3/1994 |
| EP | 0 686 675 A1 | 12/1995 |
| EP | 0 686 858 | 12/1995 |
| EP | 0 749 747 A1 | 12/1996 |
| EP | 0 815 836 A2 | 1/1998 |
| EP | 0921217 | 12/1998 |
| EP | 0 955 039 | 10/1999 |
| EP | 0 962 224 A2 | 12/1999 |
| EP | 1 043 018 A1 | 10/2000 |
| EP | 1 101 486 | 5/2001 |
| EP | 1 184 426 A2 | 3/2002 |
| EP | 1 217 046 A2 | 6/2002 |
| EP | 1 249 222 A1 | 10/2002 |
| EP | 1 264 562 | 12/2002 |
| EP | 1 318 184 A1 | 6/2003 |
| EP | 1 382 323 | 1/2004 |
| EP | 1 410 786 A1 | 4/2004 |
| EP | 1 411 069 A2 | 4/2004 |
| EP | 1 424 372 | 6/2004 |
| EP | 1 440 681 A1 | 7/2004 |
| EP | 1 510 502 | 3/2005 |
| EP | 1 591 035 | 11/2005 |
| EP | 2 876 011 | 4/2006 |
| FR | 2 077 143 | 10/1971 |
| FR | 2 232 303 | 1/1975 |
| FR | 2 268 512 | 11/1975 |
| FR | 2 393 573 | 1/1979 |
| FR | 2 594 130 | 8/1987 |
| FR | 2 758 697 | 7/1998 |
| FR | 2 845 277 | 4/2004 |
| FR | 2 845 899 | 4/2004 |
| FR | 2 846 277 | 4/2004 |
| FR | 2 847 812 | 6/2004 |
| FR | 2 848 821 | 6/2004 |
| FR | 2 848 826 | 6/2004 |
| FR | 2 850 271 | 7/2004 |
| FR | 2 851 463 | 8/2004 |
| GB | 1331819 | 9/1973 |
| GB | 1 510 674 | 5/1978 |
| GB | 2355987 A | 5/2001 |
| JP | 51-10959 | 4/1976 |
| JP | 51-137733 A | 11/1976 |
| JP | S-55-81809 | 6/1980 |
| JP | A-56-152411 | 11/1981 |
| JP | A-58-206610 | 12/1983 |
| JP | A-61-112008 | 5/1986 |
| JP | 63-175670 A | 7/1988 |
| JP | A-1-242513 | 9/1989 |
| JP | A-1-294611 | 11/1989 |
| JP | A-2-111340 | 4/1990 |
| JP | A-04-108710 | 8/1990 |
| JP | A-3-284613 | 12/1991 |
| JP | A-3-286463 | 12/1991 |
| JP | A-4-198117 | 7/1992 |
| JP | A-4-292664 | 10/1992 |
| JP | A-5-17710 | 1/1993 |
| JP | A-7-258460 | 10/1995 |
| JP | A-7-304633 | 11/1995 |
| JP | A-7-304997 | 11/1995 |
| JP | A-7-316015 | 12/1995 |
| JP | A-7-324015 | 12/1995 |
| JP | A-7-331109 | 12/1995 |
| JP | 8-38992 | 2/1996 |
| JP | A-8-127513 | 5/1996 |
| JP | A-9-188830 | 7/1997 |
| JP | A-10-87437 | 4/1998 |
| JP | A-10-158450 | 6/1998 |
| JP | A-10-158541 | 6/1998 |
| JP | A-2000-143490 | 11/1998 |
| JP | A-11-012493 | 1/1999 |
| JP | A-11-113631 | 4/1999 |
| JP | A-11-181329 | 7/1999 |
| JP | A-11-236312 | 8/1999 |
| JP | A-2000-168667 | 6/2000 |
| JP | A-2000-345096 | 12/2000 |
| JP | A-2001-61550 | 3/2001 |
| JP | A-2001-270805 | 10/2001 |
| JP | A-2001-302432 | 10/2001 |
| JP | A-2002-114641 | 4/2002 |
| JP | A-2002-138010 | 5/2002 |
| JP | A-2002-188021 | 7/2002 |
| JP | A-2002-194349 | 7/2002 |
| JP | A-2002-363440 | 12/2002 |
| JP | A-2003-000338 | 1/2003 |
| JP | A-2003-2634 | 1/2003 |
| JP | A-2003-24133 | 1/2003 |
| JP | A-2003-55575 | 2/2003 |
| JP | A-2003-125846 | 5/2003 |
| JP | A-2003-128932 | 5/2003 |
| JP | A-2003-160438 | 6/2003 |
| JP | A-2003-199620 | 7/2003 |
| JP | WO 2004/009004 | 1/2004 |
| JP | A-2004-043367 | 2/2004 |
| JP | A-2004-043656 | 2/2004 |
| JP | A-2004-059746 | 2/2004 |
| JP | A-2004-123681 | 4/2004 |
| JP | A-2004-131484 | 4/2004 |
| JP | A-2004-512348 | 4/2004 |
| JP | A-2004-137280 | 5/2004 |
| JP | A-2004-231610 | 8/2004 |
| JP | A-2004-307424 | 11/2004 |
| JP | A-2005-68323 | 3/2005 |
| JP | A-2005-516890 | 6/2005 |
| JP | A-2005-232152 | 9/2005 |
| WO | WO 93/23009 | 11/1993 |
| WO | WO 93/23446 | 11/1993 |
| WO | WO 93/23446 A2 | 11/1993 |
| WO | WO 94/26729 | 11/1994 |
| WO | WO 95/00578 | 1/1995 |
| WO | WO 95/03776 | 2/1995 |
| WO | WO 95/06078 | 3/1995 |
| WO | WO 95/23537 | 9/1995 |
| WO | WO 96/19347 | 6/1996 |
| WO | WO 97/35541 | 10/1997 |
| WO | WO 99/32076 | 7/1999 |
| WO | WO 99/36477 | 7/1999 |
| WO | WO 99/36478 | 7/1999 |
| WO | WO 01/38222 A1 | 5/2001 |
| WO | WO 02/28356 | 4/2002 |
| WO | WO 02/053114 | 7/2002 |
| WO | WO 03/016429 A1 | 2/2003 |
| WO | WO 03/020225 A1 | 3/2003 |
| WO | WO 03020255 A1 | 3/2003 |
| WO | WO 04/000244 | 12/2003 |
| WO | WO 2004/007096 | 1/2004 |
| WO | WO 2004/026972 A1 | 4/2004 |
| WO | WO 2004/028488 | 4/2004 |
| WO | WO 2004/028490 A2 | 4/2004 |
| WO | WO 2006/027494 | 3/2006 |
| WO | WO 2006/037900 | 4/2006 |
| WO | WO 2006/037902 A1 | 4/2006 |
| WO | WO 2006/037903 | 4/2006 |

(56) References Cited

FOREIGN PATENT DOCUMENTS

WO    WO 2006/037906    4/2006
WO    WO 2006/054002    5/2006

OTHER PUBLICATIONS

Blakely, Richard J.; "Potential Theory in Gravity and Magnetic Applications," 1996, Cambridge University Press; pp. 87-90.*
Drahl, Carmen; "Nail Polish", 2008, American Chemical Society, Chemical & Engineering News, vol. 86, No. 32, p. 32 (pp. 1-2 as supplied).*
Merriam-Webster™ "Merriam-Webster's Collegiate Dictionary, 11th edition," 2003; Merriam-Websters Inc; entry for "cosmetic," pp. 1-20.*
21-USC-Chapter-9-subchapter -II, definition of "cosmetic," p. 32.*
Kurtus, Ron; "Detection of a Magnetic Field," dated May 23, 2004, as captured by internet archive ( ) on Jun. 4, 2004 from science/magnetic_detection.htm>, pp. 1-5 as provided.*
Roeben, Scott; "Ferreting Out Funny Money: Fighting Counterfeiting," as captured by interet archive ( ) on Feb. 3, 2004 from subpages/counterfeit.htm>, pp. 1-7 as provided.*
Dye, Renee; "The Buzz on Buzz," Harvard Business Review, Nov.-Dec. 2000, issue, pp. 139-146.*
Kurtus, Ron; "Detection of a Magnetic Field," dated May 23, 2004, as captured by internet archive ( ) on Jun 4, 2004 from science/magnetic_detection.htm>, pp. 1-5 as provided.*
Roeben, Scott; "Ferreting Out Funny Money: Fighting Counterfeiting," as captured by interet archive ( ) on Feb 3, 2004 from subpages/counterfeit.htm>, pp. 1-7 as provided.*
Furst, E.M. et al., "Permanently Linked Monodisperse Paramagnetic Chains," Langmuir 14(26): 7334-36, Nov. 26, 1998.
Pradyot Patnaik, Handbook of Inorganic Chemicals (2003), p. 945.
Oct. 19, 2009 Office Action issued in U.S. Appl. No. 11/663,776.
Oct. 21, 2009 Office Action issued in U.S. Appl. No. 11/664,003.
Oct. 27, 2009 Office Action issued in U.S. Appl. No. 11/663,977.
Oct. 27, 2009 Office Action issued in U.S. Appl. No. 11/663,978.
Furst, E.M. et al., "Permanently Linked Monodisperse Paramagnetic Chains," Longmuir 14(26): 7334-36, Nov. 26, 1998.
Hansen, C.M., "Three Dimensional Solubility Parameter—Key to Paint Component Affinities: I. Solvents, Plasticizers, Polymers, and Resins," J. Paint Tech. 39(505): 104-117 (1967).
Fermigier, et al., "Suspensions de particules magnetiques," Bulletin of the SFP (105): pp. 3-5, Jul. 1996.
Goubault, C., "Flexible Magnetic Filaments as Micromechanical Sensors, "Physical Review Letters 91(26): 260802-1-260802-4 (2003).
"Graft Copolymers with Short Side Chains," Polymer Letters, 1967, vol. 5, pp. 477-481.
Goubault, "Colloides magnetiques: auto-organisation et applications biologiques," Doctoral Thesis of the University of Paris VI, Mar. 23, 2004.
U.S. Appl. No. 11/663,977, filed Mar. 28, 2007, Ludovic Thevenet et al.
U.S. Appl. No. 11/664,003, filed Aug. 16, 2007, Ludovic Thevenet.
U.S. Appl. No. 11/663,975, filed Aug. 16, 2007, Ludovic Thevenet.
U.S. Appl. No. 11/663,776, filed Aug. 16, 2007, Ludovic Thevenet.
U.S. Appl. No. 11/663,978, filed Aug. 16, 2007, Ludovic Thevenet.
French Search Report for French Patent Application No. FR 04/50712, priority document for co-pending U.S. Appl. No. 11/100,513, Nov. 9, 2004.
French Search Report for French Patent Application No. FR 04/50713, priority document for co-pending U.S. Appl. No. 11/100,566, Nov. 23, 2004.
French Search Report for French Patent Application No. FR 04/50714, priority document for co-pending U.S. Appl. No. 11/100,509, Nov. 10, 2004.
French Search Report for French Patent Application No. FR 04/50715, priority document for co-pending U.S. Appl. No. 11/100,514, Nov. 23, 2004.

Aug. 4, 2010 Office Action issued in U.S. Appl. No. 11/663,978.
Oct. 17, 2008 Chinese Office Action issued in Chinese Patent Application No. 200610111595.3.
Aug. 4, 2010 Office Action issued in U.S. Appl. No. 11/663,977.
International Search Report for PCT Application No. PCT/IB03/04306, priority document for co-pending U.S. Appl. No. 10/529,872, dated Mar. 3, 2004.
International Search Report for PCT/FR2005/050557, priority document for co-pending U.S. Appl. No. 11/242,901, Feb. 10, 2006.
Dec. 28, 2006 Office Action issued in U.S. Appl. No. 11/100,509.
U.S. Appl. No. 11/242,900, filed Oct. 5, 2005, Ludovic Thevenet.
U.S. Appl. No. 11/242,901, filed Oct. 5, 2005, Ludovic Thevenet.
U.S. Appl. No. 11/482,165, filed Jul. 7, 2006, Ludovic Thevenet.
U.S. Appl. No. 11/511,324, filed Aug. 9, 2006, Marc Ramet.
U.S. Appl. No. 11/922,411, filed Jun. 17, 2008, Ludovic Thevenet.
Apr. 13, 2006 French Search Report issued in FR 0552125.
May 14, 2009 Office Action issued in U.S. Appl. No. 11/482,165.
Dec. 10, 2008 Office Action issued in U.S. Appl. No. 11/482,165.
Feb. 11, 2009 Office Action issued in U.S. Appl. No. 11/663,978.
Jun. 9, 2010 Office Action issued in U.S. Appl. No. 11/664,003.
Jul. 23, 2010 Office Action issued in U.S. Appl. No. 11/663,975.
U.S. Appl. No. 10/529,872, filed Oct. 12, 2005, Christophe Dumousseaux.
U.S. Appl. No. 11/100,509, filed Apr. 7, 2005, Christophe Dumousseaux.
U.S. Appl. No. 11/100,513, filed Apr. 7, 2005, Christophe Dumousseaux.
U.S. Appl. No. 11/100,514, filed Apr. 7, 2005, Xavier Blin.
U.S. Appl. No. 11/100,566, filed Apr. 7, 2005, Christophe Dumousseaux.
U.S. Appl. No. 11/101,398, filed Apr. 8, 2005, Christophe Dumousseaux.
U.S. Appl. No. 11/101,399, filed Apr. 8, 2005, Christophe Dumousseaux.
U.S. Appl. No. 11/101,400, filed Apr. 8, 2005, Christophe Dumousseaux.
U.S. Appl. No. 11/770,177, filed Jun. 28, 2007, Christophe Dumousseaux.
Aug. 16, 2007 Office Action issued in U.S. Appl. No. 11/101,400.
Aug. 12, 2009 Restriction Requirement issued in U.S. Appl. No. 11/663,977.
Jan. 15, 2009 Office Action issued in U.S. Appl. No. 11/100,514.
Jan. 21, 2010 Office Action issued in U.S. Appl. No. 11/242,901.
Jan. 22, 2009 Office Action issued in U.S. Appl. No. 11/101,400.
Jan. 27, 2009 Office Action issued in U.S. Appl. No. 11/770,177.
Jan. 7, 2009 Office Action issued in U.S. Appl. No. 11/100,566.
Jan. 8, 2009 Office Action issued in U.S. Appl. No. 11/242,901.
Jul. 10, 2009 Office Action issued in U.S. Appl. No. 11/770,177.
Jul. 7, 2009 Office Action issued in U.S. Appl. No. 11/242,901.
Jul. 9, 2009 Office Action issued in U.S. Appl. No. 11/100,566.
Jun. 23, 2008 Office Action issued in U.S. Appl. No. 11/101,399.
Jun. 23, 2008 Office Action issued in U.S. Appl. No. 11/242,901.
Jun. 24, 2008 Office Action issued in U.S. Appl. No. 11/100,566.
Jun. 24, 2008 Office Action issued in U.S. Appl. No. 11/770,177.
Jun. 26, 2008 Office Action issued in U.S. Appl. No. 11/101,398.
Mar. 19, 2009 Office Action issued in U.S. Appl. No. 11/101,398.
Mar. 19, 2009 Office Action issued in U.S. Appl. No. 11/101,399.
Mar. 20, 2008 Office Action issued in U.S. Appl. No. 11/101,400.
May 21, 2009 Office Action issued in U.S. Appl. No. 11/100,513.
Nov. 9, 2009 Office Action issued in U.S. Appl. No. 11/101,400.
Oct. 1, 2009 Office Action issued in U.S. Appl. No. 11/101,398.
Oct. 26, 2009 Office Action issued in U.S. Appl. No. 11/100,513.
Sep. 24, 2009 Office Action issued in U.S. Appl. No. 11/101,399.
Titanium Dioxide—Wikipedia (http://en.wikipedia.org/wikilTitanium_dioxide.retrieved online on Aug. 10, 2010).
Apr. 27, 2010 Office Action issued in U.S. Appl. No. 11/770,177.
Apr. 28, 2010 Office Action issued in U.S. Appl. No. 11/100,566.
Aug. 26, 2009 Office Action issued in U.S. Appl. No. 11/511,324.
Craft Master, advertisement, 1975.
May 31, 2006 French Search Report issued in FR 0552609.
International Cosmetic Ingredient Dictionary Handbook, 1997 Edition, pp. 371-386.

(56) References Cited

OTHER PUBLICATIONS

International Cosmetic Ingredient Dictionary Handbook, 1997 Edition, pp. 524-528.
Feb. 20, 2006 International Search Report issued in PCT/FR2005/050557.
Dec. 11, 2006 European Search Report issued in EP 06 30 0902.
Mar. 17, 2010 Office Action issued in U.S. Appl. No. 11/511,324.
Dec. 19, 2006 International Search Report issued in PCT/IB2006/052239.
Jun. 30, 2010 Office Action issued in U.S. Application No. 11/663,776.
Mar. 25, 2011 Japanese Office Action issued in Japanese Patent Application No. 2007-535205 (with translation).
Feb. 15, 2011 Japanese Office Action issued in Japanese Patent Application No. 2007-535206 (with translation).
Feb. 15, 2011 Japanese Office Action issued in Japanese Patent Application No. 2007-535204 (with translation).
Jan. 13, 2011 Japanese Office Action issued in Japanese Patent Application No. 2007-534055 (with translation).
Jan. 13, 2011 Japanese Office Action issued in Japanese Patent Application No. 2007-534056 (with translation).
Sep. 16, 2010 Office Action issued in U.S. Appl. No. 11/511,324.
May 24, 2011 Office Action issued in U.S. Appl. No. 11/922,411.
Notice of the Reasons for Rejection for corresponding Japanese Patent Application No. 2007-535207, mailed Apr. 4, 2011 (with English translation).
Jan. 18, 2011 Restriction Requirement issued in U.S. Appl. No. 11/922,411.
Feb. 11, 2011 Office Action issued in U.S. Appl. No. 11/663,776.
Dec. 28, 2010 Office Action issued in U.S. Appl. No. 11/663,975.
Dec. 28, 2010 Office Action issued in U.S. Appl. No. 11/663,977.
Dec. 27, 2010 Office Action issued in U.S. Appl. No. 11/663,978.
Feb. 11, 2011 Office Action issued in U.S. Appl. No. 11/664,003.
Japanese Office Action with English-language translation for Japanese Application No. 2007-534054 mailed Oct. 7, 2010.
Aug. 23, 2011 Office Action issued in U.S. Appl. No. 11/663,776.
Aug. 22, 2011 Office Action issued in U.S. Appl. No. 11/663,975.
Aug. 22, 2011 Office Action issued in U.S. Appl. No. 11/663,977.
Aug. 22, 2011 Office Action issued in U.S. Appl. No. 11/663,978.
Aug. 17, 2011 Office Action issued in U.S. Appl. No. 11/664,003.
Jan. 18, 2012 Office Action issued in U.S. Appl. No. 11/922,411.
Dec. 22, 2011 Office Action issued in U.S. Appl. No. 11/511,324.
Definition of "soft iron", Collins English Dictionary, $5^{th}$ edition (2000).
Office Action issued Aug. 13, 2012 in U.S. Appl. No. 11/511,324.
Office Action issued Aug. 30, 2012 in U.S. Appl. No. 11/663,776.
Office Action issued Aug. 30, 2012 in U.S. Appl. No. 11/663,978.
Office Action issued Aug. 30, 2012 in U.S. Appl. No. 11/664,003.
Office Action issued Aug. 30, 2012 in U.S. Appl. No. 11/242,901.
Office Action issued Aug. 30, 2012 in U.S. Appl. No. 11/663,977.
Kurtus, "Detection of a Magnetic Field," dated May 23, 2004, as captured by internet archive (<web.archive.org>) on Jun 4, 2004 from www.school-for-champions.com/science/magnetic_detection.htm, pp. 1-5.
Roeben, "Ferreting Out Funny Money: Fighting Counterfeiting," as captured by internet archive (<web.archive.org>) on Feb 3, 2004 from <dribbleglass.com/subpages/counterfeit.htm>, pp. 1-7.
Apr. 12, 2012 Office Action issued in U.S. Appl. No. 11/663,978.
Mar. 29, 2012 Office Action issued in U.S. Appl. No. 11/663,975.
Apr. 4, 2012 Office Action issued in U.S. Appl. No. 11/663,776.
Apr. 12, 2012 Office Action issued in U.S. Appl. No. 11/663,977.
Apr. 6, 2012 Office Action issued in U.S. Appl. No. 11/664,003.
Jan. 19, 2012 Japanese Office Action issued in Japanese Patent Application No. 2008-520040 (with translation).
Oct. 2, 2015 Office Action issued in U.S. Appl. No. 13/777,573.
Merriam-Webster's Collegiate Dictionary, 11th ed., 2004, entry for "manual," p. 757.
May 13, 2016 Office Action issued in U.S. Appl. No. 13/777,573.

\* cited by examiner

METHOD OF APPLYING MAKEUP BY MEANS OF A MAGNETIC COMPOSITION INCLUDING AT LEAST ONE INTERFERENTIAL PIGMENT The present invention relates to a method of applying makeup to a natural surface, such as the skin, the nails, hair, or the lips, or to an artificial surface, such as false nails, and it also relates to a kit for implementing such a method.

A need exists to benefit from novel appearance effects in the field of makeup and the invention seeks to satisfy that need.

A METHOD OF APPLYING MAKEUP

According to one of its aspects, the invention provides a method of applying makeup to keratinous substances, in particular the skin, the lips, the nails, or hair, the method comprising:
  depositing at least one cosmetic composition on the surface to be made up, the cosmetic composition comprising:
    at least one body that presents non-zero magnetic susceptibility and that is movable under the effect of a magnetic field; and
    at least one interferential pigment; and
  exposing at least part of the composition to a magnetic field, so as to modify the orientation and/or displace at least some of the magnetic bodies.

The magnetic bodies may be different from the diffractive pigment, or, in a variant, the diffractive pigment may constitute all or some of the magnetic bodies.

When the magnetic bodies contribute color, a change in their orientation under the effect of the magnetic field may lead to a change in the appearance of the composition.

When the magnetic bodies are displaced, the shape of the deposit of composition may be affected, thereby enabling a portion in relief to be created, for example.

The composition need not be exposed to the magnetic field while the composition is being applied. The magnetic field may be exerted after the composition has been applied.

The magnetic field may be applied so as to form at least one pattern on the composition, said pattern being linked to the shape of the field lines, for example.

The invention thus makes it possible to create novel makeup effects with a cosmetic composition, enabling patterns in relief to be produced, for example, or imparting an impression of relief or various other possibly geometrical patterns.

The magnetic field may also be applied so as to model the clarity and/or the color of at least a region of the face or of the body to which the composition has been applied.

For example, when the cosmetic composition is a foundation, orienting the magnetic bodies under the effect of the magnetic field makes it possible to modify the clarity of the composition and thus to model the appearance of the face in the regions exposed to the magnetic field, in particular so as to apply makeup of cameo type, without sharp transitions between the light regions and the dark regions if so desired. By way of example, the magnetic field may be applied so as to darken the sides of the face, so as to make it appear thinner than it really is.

In an implementation of the invention, a layer of a second cosmetic composition is applied to the first containing the magnetic bodies with a view to obtaining a depth, gloss, smoothness, or other effect, for example. The second composition may be transparent and may optionally be colored. By way of example, the second composition may be for application to the lips or to the nails. The second composition may also be applied to the surface before the first composition, so as to create a colored base, or so as to improve the retention and/or the comfort of the first composition, for example.

The magnetic field may be applied until the composition containing the magnetic bodies obtains a fixed appearance, i.e. the appearance of said composition ceases to vary even if the magnetic field continues to exist. In a variant, the magnetic field may be applied for a period of time that is shorter than the period of time that causes all of the magnetic bodies in the exposed region to be permanently displaced and/or oriented.

Since the clarity and/or the color of the first composition change progressively under the effect of the magnetic field, the user can stop subjecting the magnetic bodies to the field when the first composition presents the desired appearance.

The magnetic field may be exerted successively on different regions of the surface that are coated with the composition.

The magnetic field may be exerted on regions of the surface that are disjoint, so as to create separate patterns, for example.

A region of the surface coated with the composition need not be exposed to the magnetic field, so as not to modify the appearance of the composition in said region after it has been deposited.

Two regions of the surface may be exposed unequally to the magnetic field.

The composition may be applied in various ways, e.g. by means of a cosmetics applicator that is preferably non-magnetic and that is selected from brushes, flocked endpieces, foams, woven fabrics, non-woven fabrics, brushes, or combs, for example, or it may be applied without using an applicator, with the composition being spread on with the fingers, or sprayed on, for example.

In an implementation of the invention, the composition is applied to the surface through a perforated mask. This makes it possible to produce a predetermined pattern corresponding to the shape of the perforation, for example. At least one region of the surface covered in the first composition may then be exposed to the magnetic field.

After a given drying time, the composition may take on a state that prevents the magnetic bodies from further changing their orientation under the effect of a magnetic field. This applies to a nail varnish, for example. In some circumstances, the orientation of the magnetic particles may also be modified at any time, in particular when the first composition does not dry, or presents a very long drying time. This may apply to a foundation, for example.

The magnetic bodies may be presented in various forms.

MAGNETIC BODIES

The expression "magnetic bodies" must not be understood in limiting manner and covers particles, fibers, or clumps of particles and/or fibers, of any shape, presenting non-zero magnetic susceptibility.

The concentration of magnetic bodies in the composition lies in the range about 0.05% to about 50% by weight, for example, in particular in the range about 0.1% to about 40% by weight, better in the range 1% to about 30% by weight.

The applied composition may include magnetic fibers or other aspherical bodies, such as chains of particles or of fibers.

In the absence of a magnetic field, the magnetic bodies preferably do not present any remanent magnetism.

The magnetic bodies may comprise any magnetic material that presents sensitivity to the lines of a magnetic field, regardless of whether the field is produced by a permanent magnet or is the result of induction, the material being selected from nickel, cobalt, iron, and alloys and oxides thereof, in particular $Fe_3O_4$, and also from gadolinium, terbium, dysprosium, erbium, and alloys and oxides thereof, for example. The magnetic material may be of the "soft" or of the "hard" type. In particular, the magnetic material may be soft iron.

The magnetic bodies may optionally present a multilayer structure including at least one layer of a magnetic material such as iron, nickel, cobalt, and alloys and oxides thereof, in particular $Fe_3O_4$, for example.

The magnetic bodies are preferably aspherical, presenting an elongate shape, for example. Thus, when the particles are subjected to the magnetic field, they tend to become oriented with their longitudinal axes in alignment with the field lines, and they are subjected to a change in orientation which results in the first composition changing in appearance.

When the magnetic bodies are substantially spherical particles, their appearance is preferably non-uniform, so that a change in orientation results in a change in appearance.

Regardless of their form, the size of the bodies may be in the range 1 nanometers (nm) to 10 millimeters (mm), for example, preferably in the range 10 nm to 5 mm, and more preferably in the range 100 nm to 1 mm, e.g. in the range 0.5 micrometers (μm) to 300 μm or 1 μm to 150 μm. The size is the size given by the statistical grain size distribution at half the population, referred to as "D50".

When the bodies are particles that do not have an elongate shape, or that have an elongate shape with a relatively small form factor, the size of the particles is less than 1 mm, for example.

The magnetic bodies are magnetic pigments, for example.

Magnetic Pigments

Particularly suitable pigments are nacres comprising iron oxide $Fe_3O_4$. By way of example, pigments presenting magnetic properties are those sold under the trade names COLORONA BLACKSTAR BLUE, COLORONA BLACKSTAR GREEN, COLORONA BLACKSTAR GOLD, COLORONA BLACKSTAR RED, CLOISONNE NU ANTIQUE SUPER GREEN, MICRONA MATTE BLACK (17437), MICA BLACK (17260), COLORONA PATINA SILVER (17289), and COLORONA PATINA GOLD (117288) by MERCK, or indeed FLAMENCO TWILIGHT RED, FLAMENCO TWILIGHT GREEN, FLAMENCO TWILIGHT GOLD, FLAMENCO TWILIGHT BLUE, TIMICA NU ANTIQUE SILVER 110 AB, TIMICA NU ANTIQUE GOLD 212 GB, TIMICA NU-ANTIQUE COPPER 340 AB, TIMICA NU ANTIQUE BRONZE 240 AB, CLOISONNE NU ANTIQUE GREEN 828 CB, CLOISONNE NU ANTIQUE BLUE 626 CB, GEMTONE MOONSTONE G 004, CLOISONNE NU ANTIQUE RED 424 CHROMA-LITE, BLACK (4498), CLOISONNE NU ANTIQUE ROUGE FLAMBE (code 440 XB), CLOISONNE NU ANTIQUE BRONZE (240 XB), CLOISONNE NU ANTIQUE GOLD (222 CB), and CLOISONNE NU ANTIQUE COPPER (340 XB) by ENGELHARD.

Still by way of example of a magnetic pigment that is suitable for being used in the formulation of the composition, mention may be made of black iron oxide particles, e.g. those sold under the trade name SICOVIT noir E172 by BASF.

Magnetic pigments may also comprise metallic iron, in particular passivated soft iron, e.g. obtained from carbonyl iron by implementing the method described in U.S. Pat. No. 6,589,331, the contents of which are incorporated herein by reference. The particles may include a surface oxide layer.

Soft-iron based particles are sold in particular under the trade name STAPA® WM IRON VP 041040 by ECKART.

Magnetic Fibers

The term "fibers" means generally elongate bodies presenting, for example, a form factor in the range 3.5 to 2500 or 5 to 500, e.g. 5 to 150. The form factor is defined by the ratio L/D, where L is the length of the fiber and D is the diameter of the circle in which the widest cross-section of the fiber is inscribed.

By way of example, the cross-section of the fibers may be inscribed in a circle having a diameter in the range 2 nm to 500 μm, e.g. in the range 100 nm to 100 μm, or even 1 μm to 50 μm.

By way of example, the fibers may present a length in the range 1 μm to 10 mm, e.g. 0.1 mm to 5 mm, or even 0.3 mm to 3.5 mm.

By way of example, the fibers may present a weight in the range 0.15 denier to 30 denier (weight in grams for 9 km of thread), e.g. 0.18 denier to 18 denier.

The cross-section of the fibers may be of any shape, e.g. circular, or polygonal, in particular square, hexagonal, or octagonal.

The composition may contain solid or hollow fibers that may be independent or interlinked, e.g. braided.

The composition may contain fibers having ends that are blunted and/or rounded, e.g. by polishing.

The shape of the fibers need not be significantly modified when they are inserted into the composition, with said fibers being initially rectilinear and sufficiently rigid to keep their shape. In a variant, the fibers may present flexibility that enables them to be substantially deformed within the composition.

The fibers may contain a non-zero amount, that may be as great as 100%, of a magnetic material selected from soft magnetic materials, hard magnetic materials, in particular based on iron, zinc, nickel, cobalt, or manganese, and alloys and oxides thereof, in particular $Fe_3O_4$, rare earths, barium sulfate, iron-silicon alloys, possibly containing molybdenum, $Cu_2MnAl$, MnBi, or a mixture thereof, this list not being limiting.

When the composition contains fibers containing magnetic particles, said magnetic particles may be present at least at the surface of the fibers, or only at the surface of the fibers, or only inside the fibers, or they may even be dispersed within the fibers in substantially uniform manner, for example.

By way of example, each fiber may include a non-magnetic core with a plurality of magnetic particles on its surface.

Each fiber may also include a synthetic matrix containing a plurality of magnetic grains dispersed therein.

Where appropriate, a synthetic material filled with magnetic particles may itself be covered by a non-magnetic membrane. By way of example, such a membrane constitutes a barrier isolating the magnetic material(s) from the surrounding environment and/or it can provide color. Each fiber may comprise a one-piece magnetic core and be covered by a non-magnetic membrane, or it may comprise a one-piece non-magnetic core and be covered by a magnetic membrane.

The composition may contain fibers made by extruding or co-extruding one or more polymeric materials, in particular thermoplastics and/or elastomers. One of the extruded materials may contain a filler of dispersed magnetic particles.

Each fiber may comprise a synthetic material selected from polyamides; polyethylene terephthalate (PET); acetates; polyolefins, in particular polyethylene (PE) or polypropylene (PP); polyvinyl chloride (PVC); polyester block amide; plasticized Rilsan®; elastomers, in particular polyester elastomers, polyethylene (PE) elastomers, silicone elastomers, nitrile elastomers; or a mixture of these materials, this list not being limiting.

The composition may contain composite fibers each comprising a magnetic core that is covered, at least in part, by at least one non-magnetic, synthetic, or natural material. By way of example, the magnetic core may be covered by co-extruding a membrane made of a non-magnetic material around the core.

The core may alternatively be covered in some other way, e.g. by polymerization in situ.

The core may be a single piece or it may include a filler of magnetic grains dispersed in a matrix.

The composition may also contain composite fibers obtained by covering a non-magnetic, synthetic, or natural core, with a synthetic material filled with magnetic particles, the core being composed of a fiber made of wood; rayon; polyamide; plant matter; or polyolefin, in particular polyethylene, Nylon®, polyimideamide, or aramid, this list not being limiting.

The composition may also contain magnetic composite particles, in particular a magnetic latex.

Magnetic Composite Particles

A magnetic composite particle is a composite material constituted by an organic or an inorganic matrix and by magnetic grains. At their surfaces and/or within themselves, the magnetic composite particles may thus include grains of a magnetic material. The composite particles may be constituted by a magnetic core covered by an organic or an inorganic matrix, or they may be constituted by an organic or an inorganic core covered by a magnetic matrix.

The magnetic composite particles include one of the above-mentioned magnetic materials, for example.

The size of the magnetic composite particles may be in the range 1 nm to 1 mm, for example, preferably in the range 100 nm to 500 µm, and more preferably in the range 500 nm to 100 µm. The term "size" means the size given by the statistical grain size distribution at half the population, referred to as "D50".

The thesis by C. GOUBAULT, dated Mar. 23, 2004, and incorporated herein by reference, refers, in chapter 1, to the prior art on the subject of magnetic composite particles, and draws up a list of preparation methods that are suitable for being used to prepare magnetic composite particles, namely separately synthesizing the magnetic grains and the matrix, synthesizing the magnetic grains in contact with the matrix, or synthesizing the matrix in the presence of the magnetic grains.

KISKER markets inorganic-matrix magnetic composite particles composed of silica. DYNAL, SERADYN, ESTAPOR, and ADEMTECH propose organic-matrix magnetic composite particles that are also suitable for being used in the invention.

More particularly, under the reference M1-070/60, ESTAPOR markets magnetic latex constituted by grains of ferrite that are evenly distributed in a polystyrene matrix, said latex including 65% iron oxide, the mean diameter of the polystyrene particles being 890 nm, and the dry material mass content being 10%.

Ferrofluid

The composition may contain a ferrofluid, i.e. a stable colloidal suspension of magnetic particles, in particular of magnetic nanoparticles.

The particles, having a size of the order of several tens of nanometers, for example, are dispersed in a solvent (water, oil, organic solvent), either by means of a surfactant or a dispersant, or by electrostatic interactions.

By way of example, the ferrofluids can be prepared by grinding ferrites or other magnetic particles until nanoparticles are obtained, which particles are then dispersed in a fluid containing a surfactant which is absorbed by the particles and stabilizes them, or else they can be prepared by precipitating a metallic-ion solution in a basic medium.

Each particle of the ferrofluid presents a magnetic moment that is determined by the size of the particle, and by the nature of the magnetic material.

Under the action of a magnetic field, the magnetic moments of the particles tend to come into alignment with the field lines, with non-zero magnetization appearing in the liquid. If the field is removed, there is no hysteresis and magnetization drops to zero.

Beyond a field threshold value, it is also possible to cause macroscopic changes in the liquid, e.g. the appearance of peaks, or a change in rheological properties.

The term "ferrofluid" also encompasses an emulsion of ferrofluid droplets in a solvent. Each drop thus contains colloidal magnetic particles in stable suspension. This makes it possible to have a ferrofluid in any type of solvent. The size of the magnetic particles in suspension in the ferrofluid may be in the range 1 nm to 10 µm, for example, preferably in the range 1 nm to 1 µm, and more preferably in the range 1 nm to 100 nm. The term "size" means the size given by the statistical grain size distribution at half the population, referred to as "D50".

Mention can be made in particular of ferrofluids sold by Liquids Research LTD under the references:

WHKS1S9 (A, B, or C), which is a water-based ferrofluid containing magnetite ($Fe_3O_4$), having particles of 10 nm in diameter.

WHJS1 (A, B, or C), which is an isoparaffin-based ferrofluid, containing magnetite ($Fe_3O_4$) particles that are 10 nm in diameter.

BKS25_dextran, which is a water-based ferrofluid stabilized by dextran, containing magnetite ($Fe_3O_4$) particles that are 9 nm in diameter.

Chains of Particles and/or of Magnetic Fibers

The composition may contain clumps of particles or fibers having a largest dimension, e.g. length, that may, for example, be in the range 1 nm to 10 mm, e.g. in the range 10 nm to 5 mm, or in the range 100 nm to 1 mm, or even in the range 0.5 µm to 3.5 mm, e.g. in the range 1 µm to 150 µm. The term "size" means the size given by the statistical grain size distribution at half the population, referred to as "D50".

By way of example, chains of magnetic particles may be obtained by assembling colloidal magnetic particles, as described in the publications "Permanently linked monodisperse paramagnetic chains", by E. M. Furst, C. Suzuki, M. Fermigier, A. P. Gast, Langmuir, 14, 7334-7336 (1998), "Suspensions of magnetic particles", by M. Fermigier, Y. Grasselli, Bulletin of the SFP (105) July 1996, and "Flexible magnetic filaments as micromechanical sensors", by C. Goubault, P. Jop, M. Fermigier, J. Baudry, E. Bertrand, J.

Bibette, Phys. Rev. Lett., 91, 26, 260802-1 to 260802-4 (2003), the contents of which are incorporated herein by reference.

In particular, those articles describe how to proceed in order to obtain chains of magnetic-latex particles that include a polystyrene matrix containing grains of iron oxide with functions on the surface, and that are bonded together in permanent manner following a chemical reaction, in particular covalent bonds between the surfaces of adjacent particles; a method is also described of obtaining chains of ferrofluid-emulsion droplets that are bonded together by physical interactions. The length and the diameter of the permanent chains obtained in this way can be controlled. Such magnetic chains constitute anisotropic magnetic objects that can be oriented and displaced under the effect of a magnetic field.

The dimensions of the magnetic chains may satisfy the same conditions as for the magnetic fibers.

INTERFERENTIAL PIGMENT

In an aspect of the invention, the composition includes at least one interferential pigment.

The expression "interferential pigment" means a pigment that is capable of producing a color by an interference phenomenon, e.g. between the light reflected by a plurality of superposed layers of different refractive indices, in particular a succession of layers of high and low refractive indices.

Within the composition, the interferential pigment can be in a proportion by weight lying in the range 0.1% to 75%, and preferably 0.5% to 70%.

By way of example, the proportion could be greater in an eyeshadow than in a nail varnish.

By way of example, an interferential pigment may include more than four layers of different refractive indices.

The layers of interferential pigment may optionally surround a core, which may present an optionally flat shape.

Nacres are examples of interferential pigments.

Nacres

The term "nacre" means colored particles of any form, which may optionally be iridescent, as produced in the shells of certain mollusks, or which are synthesized, and which exhibit a "pearlescent" coloring effect by optical interference.

As examples of nacres, mention can be made of nacre pigments such as mica titanium coated with iron oxide, mica coated with bismuth oxychloride, mica titanium coated with chromium oxide, mica titanium coated with an organic colorant, in particular of the type mentioned above, and nacre pigments based on bismuth oxychloride. They may also be particles of mica on the surface of which at least two successive layers of metal oxides and/or organic coloring substances have been superimposed.

More particularly, the nacres may have a yellow, pink, red, bronze, orangey, brown, gold, and/or coppery color or glint.

Illustrative examples of nacres suitable for being introduced as an interferential pigment into the first composition and that may be mentioned are gold color nacres, in particular those sold by ENGELHARD under the trade names Brillant gold 212G (Timica), Gold 222C (Cloisonne), Sparkle gold (Timica), Gold 4504 (Chromalite), and Monarch gold 233X (Cloisonne); bronze nacres, in particular those sold by MERCK under the trade names Bronze fine (17384) (Colorona) and Bronze (17353) (Colorona), and by ENGELHARD under the trade name Super bronze (Cloisonne); orange nacres especially those sold by ENGELHARD under the trade names Orange 363C (Cloisonne) and Orange MCR 101 (Cosmica), and by MERCK under the trade names Passion orange (Colorona) and Matte orange (17449) (Microna); brown-tinted nacres sold by ENGELHARD under the trade names Nu-antique copper 340XB (Cloisonne) and Brown CL4509 (Chromalite); nacres with a copper glint sold by ENGELHARD under the trade name Copper 340A (Timica); nacres with a red glint, especially those sold by MERCK under the trade name Sienna fine (17386) (Colorona); nacres with a yellow glint, especially those sold by ENGELHARD under the trade name Yellow (4502) (Chromalite); red-tinted nacres with gold glints, especially those sold by ENGELHARD under the trade name Sunstone G012 (Gemtone); pink nacres, especially those sold by ENGELHARD under the trade name Tan opale G005 (Gemtone); black nacres with a glint, especially those sold by ENGELHARD under the trade name Nu antique bronze 240 AB (Timica); blue nacres, especially those sold by MERCK under the trade name Matte blue (17433) (Microna); white nacres with silvery glints, especially those sold by MERCK under the trade name Xirona Silver; and orange-pink green-gold highlight nacres sold by MERCK under the trade names Indian summer (Xirona) and mixtures thereof.

At least one of the layers of the interferential pigment may include a magnetic material, thereby imparting non-zero magnetic susceptibility to the pigment. At least some, or indeed all, of the magnetic bodies may thus be constituted by particles of the interferential pigment.

As examples of interferential pigments presenting non-zero magnetic susceptibility, mention can be made of some nacres containing iron oxide $Fe_3O_4$.

By way of example, interferential pigments presenting magnetic properties are those sold under the trade names COLORONA BLACKSTAR BLUE, COLORONA BLACKSTAR GREEN, COLORONA BLACKSTAR GOLD, COLORONA BLACKSTAR RED, CLOISONNE NU ANTIQUE SUPER GREEN, MICRONA MATTE BLACK (17437), MICA BLACK (17260), COLORONA PATINA SILVER (17289), and COLORONA PATINA GOLD (117288) by MERCK, or indeed FLAMENCO TWILIGHT RED, FLAMENCO TWILIGHT GREEN, FLAMENCO TWILIGHT GOLD, FLAMENCO TWILIGHT BLUE, TIMICA NU ANTIQUE SILVER 110 AB, TIMICA NU ANTIQUE GOLD 212 GB, TIMICA NU-ANTIQUE COPPER 340 AB, TIMICA NU ANTIQUE BRONZE 240 AB, CLOISONNE NU ANTIQUE GREEN 828 CB, CLOISONNE NU ANTIQUE BLUE 626 CB, GEMTONE MOONSTONE G 004, CLOISONNE NU ANTIQUE RED 424 CHROMA-LITE, BLACK (4498), CLOISONNE NU ANTIQUE ROUGE FLAMBE (code 440 XB), CLOISONNE NU ANTIQUE BRONZE (240 XB), CLOISONNE NU ANTIQUE GOLD (222 CB), and CLOISONNE NU ANTIQUE COPPER (340 XB) by ENGELHARD.

The interferential pigment may be a goniochromatic pigment which may present magnetic properties, where appropriate.

Interferential Reflective Particles

The particles may be selected from particles of synthetic substrate at least partially coated with at least one layer of at least one metal oxide selected, for example, from oxides of titanium, in particular $TiO_2$, of iron, in particular $Fe_2O_3$, of tin, or of chromium, barium sulfate, and the following materials: $MgF_2$, $CrF_3$, $ZnS$, $ZnSe$, $SiO_2$, $Al_2O_3$, $MgO$, $Y_2O_3$, $SeO_3$, $SiO$, $HfO_2$, $ZrO_2$, $CeO_2$, $Nb_2O_5$, $Ta_2O_5$, $MoS_2$, and their mixtures or alloys.

Examples of such particles that may be mentioned are particles comprising a substrate of synthetic mica coated with titanium dioxide, or glass particles coated either with brown iron oxide, titanium oxide, tin oxide, or one of their mixtures such as those sold under the trade name REFLECKS® by ENGELHARD.

Goniochromatic Pigment

The term "goniochromatic pigment" as used in the context of the present invention means a pigment that makes it possible, when the composition is spread on a surface, to obtain a color path in the a*b* plane of the 1976 CIE color space which corresponds to a variation Dh° of the hue angle h° of at least 20° when the angle of observation is varied relative to the normal in the range 0° to 80° for light at an angle of incidence of 45°.

By way of example, the color path may be measured by means of a spectrogonioreflectometer, from INSTRUMENT SYSTEMS and referenced GON 360 GONIOMETER, after the first composition has been spread in the fluid state to a thickness of 300 μm by means of an automatic spreader on a contrast card from ERICHSEN and referenced Typ 24/5, the measurements being performed on the black background of the card.

By way of example, the goniochromatic pigment may be selected from multilayer interference structures and liquid crystal coloring agents.

By way of example, a multilayer structure may comprise at least two layers, each layer being produced, for example, from at least one material selected from the group constituted by the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, alloys, polymers, and combinations thereof.

The multilayer structure may optionally be symmetrical with respect to a central layer as regards the chemical nature of the stacked layers. Depending on the thickness and nature of the various layers, different effects are obtained.

Examples of symmetrical multilayer interference structures are as follows: $Fe_2O_3/SiO_2/Fe_2O_3/SiO_2/Fe_2O_3$, a pigment having this structure being sold under the trade name SICOPEARL by BASF; $MoS_2/SiO_2$/mica-oxide/$SiO_2$/$MoS_2$; $Fe_2O_3/SiO_2$/mica-oxide/$SiO_2/Fe_2O_3$; $TiO_2/SiO_2/TiO_2$ and $TiO_2/Al_2O_3/TiO_2$, pigments with these structures being sold under the trade name XIRONA by MERCK (Darmstadt).

By way of example, liquid crystal coloring agents comprise silicones, or cellulose ethers onto which mesomorphic groups have been grafted. Examples of suitable liquid crystal goniochromatic particles are those sold by CHENIX, and those sold under the trade name HELICONE® HC by WACKER.

Suitable goniochromatic pigments are some nacres; pigments having effects on synthetic substrates, in particular alumina, silica, borosilicate, iron oxide, or aluminum type substrates; or holographic interference flakes coming from a polyterephthalate film.

The material may further contain dispersed goniochromatic fibers. Such fibers could present a length that is less than 80 μm, for example.

The composition containing the magnetic particles may contain at least one diffractive pigment.

DIFFRACTIVE PIGMENTS

The term "diffractive pigment" as used in the context of the present invention means a pigment that is capable of producing a variation in color depending on the angle of observation when lit by white light, because of the presence of a structure which diffracts the light. Such a pigment is also sometimes referred to as a holographic pigment.

A diffractive pigment may include a diffraction grating that is capable of diffracting an incident ray of monochromatic light in defined directions.

The diffraction grating may comprise a periodic pattern, in particular a line, with the distance between two adjacent patterns being the same as the wavelength of the incident light.

When the incident light is polychromatic, the diffraction grating separates the various spectral components of the light and produces a rainbow effect.

With regard to the structure of diffractive pigments, reference can usefully be made to the article "Pigments Exhibiting Diffractive Effects" by Alberto Argoitia and Matt Witzman, 2002, Society of Vacuum coaters, $45^{th}$ Annual Technical Conference Proceedings 2002.

The diffractive pigment may be made with patterns having various profiles, in particular triangular, optionally symmetrical, notched, of optionally constant width, sinusoidal, or stepped.

The spatial frequency of the grating and the depth of the patterns are selected as a function of the degree of separation of the various desired orders. The frequency may be in the range 500 lines per mm to 3000 lines per mm, for example.

Each of the particles of the diffractive pigment preferably presents a flat shape, and in particular a wafer shape.

A single pigment particle may include two crossed diffraction gratings that are optionally perpendicular, and that optionally have the same ruling.

The diffractive pigment may present a multilayer structure comprising a layer of reflective material that is covered on at least one side by a layer of dielectric material. The dielectric material may make the diffractive pigment stiffer and longer lasting. For example, the dielectric material may thus be selected from the following materials: $MgF_2$, $SiO_2$, $Al_2O_3$, $AlF_3$, $CeF_3$, $LaF_3$, $NdF_3$, $SmF_2$, $BaF_2$, $CaF_2$, LiF, and combinations thereof. For example, the reflective material may be selected from metals and alloys thereof, and also from non-metallic reflective materials: Metals that may be used include Al, Ag, Cu, Au, Pt, Sn, Ti, Pd, Ni, Co, Rd, Nb, Cr, and materials, combinations, alloys thereof and their doping by rare earths.

Such a reflective material may, on its own, constitute the diffractive pigment which then comprises a single layer.

In a variant, the diffractive pigment may include a multilayer structure comprising a core of dielectric material with a reflective layer covering at least one side, or indeed completely encapsulating, the core. A layer of dielectric material may also cover the reflective layer(s). The dielectric material used is thus preferably inorganic, and may, for example, be selected from metal fluorides, metal oxides, metal sulfides, metal nitrides, metal carbides, and combinations thereof. The dielectric material may be in the crystalline, semi-crystalline, or amorphous state.

In this configuration, the dielectric material may, for example, be selected from the following materials: $MgF_2$, SiO, $SiO_2$, $Al_2O_3$, $TiO_2$, WO, AlN, BN, $B_4C$, WC, TiC, TiN, $N_4Si_3$, ZnS, glass particles, diamond-type carbons, and combinations thereof.

In a variant, the diffractive pigment may be composed of a preformed dielectric or ceramic material such as a naturally lamellar mineral, e.g. mica peroskovite or talc; or synthetic platelets formed from glass, alumina, $SiO_2$, carbon, an iron oxide/mica, mica covered in BN, BC, graphite, or bismuth oxychloride, and combinations thereof.

Instead of a layer of dielectric material, other materials that improve the mechanical properties may be suitable. Such materials may include silicone, metal silicides, semiconductor materials formed from elements of groups III, IV, and V, metals having a body centered cubic crystal structure, metal-ceramic compositions or materials, semiconductor glasses, and various combinations thereof.

In particular, the diffractive pigment used may be selected from those described in US patent application No. 2003/0031870 published on Feb. 13, 2003.

A diffractive pigment may, for example, have the following structure: $MgF_2/Al/MgF_2$, a diffractive pigment having this structure being sold by FLEX PRODUCTS under the trade names SPECTRAFLAIR 1400 Pigment Silver or SPECTRAFLAIR 1400 Pigment Silver FG. The proportion by weight of $MgF_2$ may be in the range 80% to 95% of the total weight of the pigment.

Other diffractive pigments are sold under the trade names Metalure® Prismatic by ECKART®.

Other possible structures are Fe/Al/Fe or Al/Fe/Al, which present non-zero magnetic susceptibility.

By way of example, the quantity of diffractive pigment may be in the range 0.1% to 5% by weight relative to the total weight of the first composition.

By way of example, the size of the diffractive pigment may be in the range 5 μm to 200 μm, and preferably in the range 5 μm to 100 μm, e.g. in the range 5 μm to 30 μm.

The thickness of the diffractive-pigment particles may be less than or equal to 3 μm, or preferably 2 μm, e.g. about 1 μm.

OTHER COLORING AGENTS

The composition may include at least one coloring agent producing light by absorbing at least a fraction of the visible spectrum.

Such a coloring agent, producing a color by an absorption phenomenon, may be constituted by a pigment that is an optionally magnetic, organic, or inorganic, or it may be a hybrid comprising both organic material and inorganic material.

The coloring agent may optionally be a particulate compound.

Where appropriate, the particles of a single magnetic pigment constitute both the coloring agent, producing the color by an absorption phenomenon, and the magnetic bodies.

When the coloring agent includes a colorant, said colorant may be selected from amongst liposoluble and hydrosoluble colorants.

Examples of liposoluble colorants are Sudan red, D&C Red No. 17, D&C Green No. 6, β-carotene, soybean oil, Sudan brown, D&C Yellow No. 11, D&C Violet No. 2, D&C orange No. 5, and quinoline yellow.

Examples of hydrosoluble colorants are beetroot juice and methylene blue.

By way of example, the colorants may represent 0.1% to 20% by weight of the first or second composition, or even 0.1% to 6%, when present.

The coloring agents may also be a lake or an organic pigment selected from the following materials and mixtures thereof:
cochineal carmine;
the organic pigments of azo, anthraquinone, indigo, xanthene, pyrene, quinoline, triphenylmethane, or fluorane dyes;
organic lakes or insoluble salts of sodium, potassium, calcium, barium, aluminum, zirconium, strontium, titanium, or of acid dyes such as azo, anthraquinone, indigo, xanthene, pyrene, quinoline, triphenylmethane, or fluorine dyes, which dyes may comprise at least one carboxylic or sulfonic acid group.

Organic pigments that may be mentioned include those with the following denominations: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The coloring agent may be an organic lake supported by an organic support such as colophane or aluminum benzoate, for example.

Particular organic lakes that may be mentioned include those with the following denominations: D&C Red No. 2 Aluminum lake, D&C Red No. 3 Aluminum lake, D&C Red No. 4 Aluminum lake, D&C Red No. 6 Aluminum lake, D&C Red No. 6 Barium lake, D&C Red No. 6 Barium/Strontium lake, D&C Red No. 6 Strontium lake, D&C Red No. 6 Potassium lake, D&C Red No. 7 Aluminum lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminum lake, D&C Red No. 9 Barium lake, D&C Red No. 9 Barium/Strontium lake, D&C Red No. 9 Zirconium lake, D&C Red No. 10 Sodium lake, D&C Red No. 19 Aluminum lake, D&C Red No. 19 Barium lake, D&C Red No. 19 Zirconium lake, D&C Red No. 21 Aluminum lake, D&C Red No. 21 Zirconium lake, D&C Red No. 22 Aluminum lake, D&C Red No. 27 Aluminum lake, D&C Red No. 27 Aluminum/Titanium/Zirconium lake, D&C Red No. 27 Barium lake, D&C Red No. 27 Calcium lake, D&C Red No. 27 Zirconium lake, D&C Red No. 28 Aluminum lake, D&C Red No. 30 lake, D&C Red No. 31 Calcium lake, D&C Red No. 33 Aluminum lake, D&C Red No. 34 Calcium lake, D&C Red No. 36 lake, D&C Red No. 40 Aluminum lake, D&C Blue No. 1 Aluminum lake, D&C Green No. 3 Aluminum lake, D&C Orange No. 4 Aluminum lake, D&C Orange No. 5 Aluminum lake, D&C Orange No. 5 Zirconium lake, D&C Orange No. 10 Aluminum lake, D&C Orange No. 17 Barium lake, D&C Yellow No. 5 Aluminum lake, D&C Yellow No. 5 Zirconium lake, D&C Yellow No. 6 Aluminum lake, D&C Yellow No. 7 Zirconium lake, D&C Yellow No. 10 Aluminum lake, FD&C Blue No. 1 Aluminum lake, FD&C Red No. 4 Aluminum lake, FD&C Red No. 40 Aluminum lake, FD&C Yellow No. 5 Aluminum lake, FD&C Yellow No. 6 Aluminum lake.

The chemical materials corresponding to each of the organic coloring substances listed above are mentioned in the work entitled "International Cosmetic Ingredient Dictionary and Handbook", 1997 edition, pages 371 to 386 and 524 to 528, published by "The Cosmetic, Toiletry, and Fragrance Association", the contents of which are incorporated herein by reference.

The composition may contain a composite pigment including a core that is coated at least in part by a membrane.

Composite Pigments

A composite pigment may be composed of particles comprising:
- an inorganic core; and
- at least one at least partial coating of at least one organic coloring substance.

At least one binder may advantageously contribute to fixing the organic coloring substance onto the inorganic core.

The particles of composite pigment may have a variety of forms. In particular, said particles may be in the form of flakes or they may be globular, in particular spherical, and may be hollow or solid. The term "in the form of flakes" means particles for which the ratio of the largest dimension to the thickness is 5 or more.

A composite pigment may, for example, have a specific surface area in the range 1 square meter per gram ($m^2/g$) to 1000 $m^2/g$, in particular in the range about 10 $m^2/g$ to about 600 $m^2/g$, and in particular in the range about 20 $m^2/g$ to about 400 $m^2/g$. The specific surface area is the value measured using the BET (Brunauer-Emmett-Teller) method.

The proportion by weight of the core may exceed 50% relative to the total weight of the composite pigment, for example lying in the range 50% to 70%, e.g. in the range 60% to 70%.

The composite pigment may be different from an interferential pigment as described in U.S. Pat. No. 6,428,773, for example. By way of example, an interferential pigment includes a plurality of layers of constant thickness of materials selected so as to be able to produce optical interferences.

The saturation C* of the composite pigment may be greater than or equal to 30, measured in accordance with the following protocol.

Protocol for Measuring the Saturation of the Composite Pigment

The values a* and b* in the CIE L*a*b* space of the composite pigment are measured as follows:

Pure composite pigment is compacted in a rectangular dish having dimensions of 2 centimeters (cm)×1.5 cm and a depth of 3 mm, by applying pressure of 100 bars.

The values a* and b* of the compacted pigment are measured with a MINOLTA 3700d spectrophotometer, in excluded specular mode, under D65 lighting, medium aperture. Saturation is given by $C^* = (a^{*2} + b^{*2})^{1/2}$.

Inorganic Core

The inorganic core may have any form that is suitable for fixing particles of organic coloring substance, for example spherical, globular, granular, polyhedral, acicular, spindle-shaped, flattened in the form of a flake, a rice grain, or a scale, and a combination of these forms, this list not being limiting.

Preferably, the ratio of the largest dimension of the core to its smallest dimension may be in the range 1 to 50.

The inorganic core may have a mean size in the range about 1 nm to about 100 nm, or even in the range about 5 nm to about 75 nm, for example in the range about 10 nm to about 50 nm, in particular 20 nm or 25 nm.

The term "mean size" means the size given by the statistical grain size distribution at half the population, referred to as "D50". The mean size may be a number mean size determined by image analysis (electron microscopy).

The inorganic core may present a refractive index that is greater than or equal to 2, or even greater than or equal to 2.1, e.g. greater than or equal to 2.2.

The inorganic core may be formed from an optionally-magnetic material selected from a non-limiting list comprising metallic salts and metal oxides, in particular oxides of titanium, zirconium, cerium, zinc, iron, iron blue, aluminum, and chromium, aluminas, glasses, ceramics, graphite, silicas, silicates, in particular aluminosilicates and borosilicates, synthetic mica, and mixtures thereof.

Oxides of titanium, in particular $TiO_2$, of iron, especially $Fe_2O_3$, of cerium, zinc, and aluminum, silicates, in particular aluminosilicates and borosilicates, are particularly suitable.

The inorganic core may have a specific surface area, measured using the BET method, in the range about 1 $m^2/g$ to about 1000 $m^2/g$, preferably in the range about 10 $m^2/g$ to about 600 $m^2/g$, for example in the range about 20 $m^2/g$ to about 400 $m^2/g$.

The inorganic core may be colored if appropriate.

Organic Coloring Material

By way of example, the organic coloring material may comprise at least one organic pigment, e.g. at least one organic lake.

By way of example, the organic coloring material may be selected from the insoluble particulate compounds in the physiologically acceptable medium of the composition.

By way of example, the organic coloring material may comprise pigments, e.g. organic lakes or other organic coloring materials, that may be selected from the following compounds and mixtures thereof:
- cochineal carmine;
- the organic pigments of azo, anthraquinone, indigo, xanthene, pyrene, quinoline, triphenylmethane, or fluorane dyes;
- organic lakes or insoluble salts of sodium, potassium, calcium, barium, aluminum, zirconium, strontium, titanium, or of acid dyes such as azo, anthraquinone, indigo, xanthene, pyrene, quinoline, triphenylmethane, or fluorine dyes, which dyes may comprise at least one carboxylic or sulfonic acid group.

Organic pigments that may be mentioned include those with the following denominations: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The organic coloring substance may comprise an organic lake supported by an organic support such as colophane or aluminum benzoate, for example.

Particular organic lakes that may be mentioned include those with the following denominations: D&C Red No. 2 Aluminum lake, D&C Red No. 3 Aluminum lake, D&C Red No. 4 Aluminum lake, D&C Red No. 6 Aluminum lake, D&C Red No. 6 Barium lake, D&C Red No. 6 Barium/Strontium lake, D&C Red No. 6 Strontium lake, D&C Red No. 6 Potassium lake, D&C Red No. 7 Aluminum lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminum lake, D&C Red No. 9 Barium lake, D&C Red No. 9 Barium/Strontium lake, D&C Red No. 9 Zirconium lake, D&C Red No. 10 Sodium lake, D&C Red No. 19 Aluminum lake, D&C Red No. 19 Barium lake, D&C Red No. 19 Zirconium lake, D&C Red No. 21 Aluminum lake, D&C Red No. 21 Zirconium lake, D&C Red No. 22 Aluminum lake, D&C Red No. 27 Aluminum lake, D&C Red No. 27 Aluminum/Titanium/Zirconium lake, D&C Red No. 27 Barium lake, D&C Red No. 27 Calcium lake, D&C Red No. 27 Zirconium lake, D&C Red No. 28 Aluminum lake, D&C Red No. 30 lake, D&C Red No. 31 Calcium lake, D&C Red No. 33 Aluminum lake, D&C Red No. 34 Calcium lake, D&C Red No. 36 lake, D&C Red No. 40 Aluminum lake, D&C Blue No. 1 Aluminum lake, D&C Green No. 3 Aluminum lake, D&C Orange No. 4 Aluminum lake, D&C Orange No. 5 Aluminum lake, D&C Orange No. 5 Zirconium lake, D&C Orange No. 10 Aluminum lake, D&C Orange No. 17 Barium lake, D&C Yellow No. 5 Aluminum lake, D&C Yellow No. 5 Zirconium lake, D&C Yellow No. 6 Aluminum lake, D&C Yellow No. 7 Zirconium lake, D&C Yellow No. 10 Aluminum lake, FD&C Blue No. 1 Aluminum lake, FD&C Red No. 4 Aluminum lake, FD&C Red No. 40 Aluminum lake, FD&C Yellow No. 5 Aluminum lake, FD&C Yellow No. 6 Aluminum lake.

The chemical compounds corresponding to each of the organic coloring substances listed above are mentioned in the work entitled "International Cosmetic Ingredient Dictionary and Handbook", 1997 edition, pages 371 to 386 and 524 to 528, published by "The Cosmetic, Toiletry, and Fragrance Association", the contents of which are incorporated herein by reference.

The proportion by weight of organic coloring material may lie in the range about 10 parts to about 500 parts by weight per 100 parts of inorganic core, or even in the range about 20 parts to about 250 parts by weight, e.g. in the range about 40 parts to about 125 parts by weight per 100 parts of inorganic core.

The total content of organic coloring material of the composition, coming from the composite pigment and from other possible pigments, may be less than 10%, for example, relative to the total weight of the composition.

The proportion of organic coloring material may exceed 30% relative to the total weight of the composite pigment, for example lying in the range 30% to 50%, e.g. in the range 30% to 40%.

Binder

The composite-pigment binder may be of any type provided that it allows the organic coloring substance to adhere to the surface of the inorganic core.

In particular, the binder may be selected from the following non-limiting list: silicone materials, polymeric, oligomeric or similar materials, in particular from organosilanes, fluoroalkylated organosilanes and polysiloxanes, for example polymethylhydrogen siloxane, as well as a variety of coupling agents such as coupling agents based on silanes, titanates, aluminates, zirconates, and mixtures thereof.

The silicone compound may be selected from the following non limiting list:
organosilanes (1) obtained from alkoxysilanes;
polysiloxanes (2) which may optionally be modified, selected from the following non limiting list:
  modified polysiloxanes (2A) comprising at least one radical selected in particular from polyethers, polyesters and epoxy compounds (henceforth termed "modified polysiloxanes");
  polysiloxanes (2B) carrying, on one silicon atom located at the end of the polymer, at least one group selected from the following non-limiting list: carboxylic acids, alcohols, and hydroxyl groups; and
  fluoroalkylated organosilane compounds (3) obtained from fluoroalkylsilanes.

The organosilane compounds (1) may be obtained from alkoxysilane compounds represented by formula (I):

$$R^1_a SiX_{4-a} \quad (I)$$

in which:
R$^1$ represents C$_6$H$_5$—, (CH$_3$)$_2$CH—CH$_2$— or a C$_b$H$_{2b+1}$-type radical (in which $b$ lies in the range 1 to 18);
X represents CH$_3$O— or C$_2$H$_5$O—; and
$a$ lies in the range 0 to 3.

Specific examples of alkoxysilane compounds may include alkoxysilanes selected from: methyltriethoxysilane, dimethyldiethoxysilane, phenyltriethoxysilane, diphenyldiethoxysilane, methyltrimethoxysilane, dimethyldimethoxysilane, phenyltrimethoxysilane, diphenyldimethoxysilane, isobutyltrimethoxysilane, decyltrimethoxysilane, and the like, in particular from methyltriethoxysilane, phenyltriethoxysilane, methyltrimethoxysilane, dimethyldimethoxysilane, isobutyltrimethoxysilane, more preferably from methyltriethoxysilane, methyltrimethoxysilane, and phenyltriethoxysilane.

The polysiloxanes (2) may in particular have formula (II):

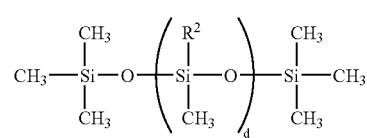

in which R$^2$ represents H— or CH$_3$— and $d$ lies in the range 15 to 450.

Polysiloxanes for which R$^2$ represents H are preferred.

The modified polysiloxanes (2A) may in particular have the following formula (III):
(a$^1$) modified polysiloxanes carrying polyethers, represented by formula (III):

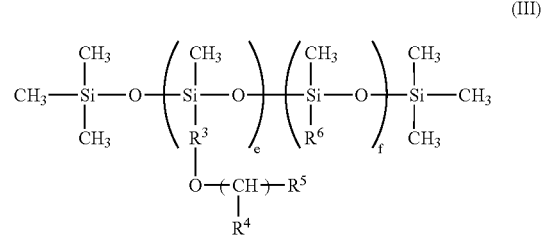

in which R$^3$ represents —(CH$_2$)$_h$—; R$^4$ represents —(CH$_2$)$_i$—CH$_3$; R$^5$ represents —OH, —COOH, —CH═CH$_2$, —C(CH$_3$)═CH$_2$ or —(CH$_2$)$_j$—CH$_3$; R$^6$ represents —(CH$_2$)$_k$—CH$_3$; $g$ and $h$ lie independently in the range 1 to 15; $j$ and $k$ lie independently in the range 0 to 15; $e$ lies in the range 1 to 50, and $f$ lies in the range 1 to 300;
(a$^2$) modified polysiloxanes carrying polyesters, represented by formula (IV):

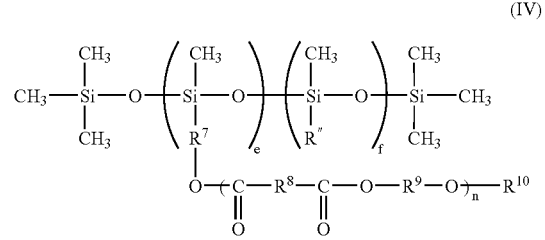

in which R$^7$, R$^{8'}$ and R$^9$ independently represent —(CH$_2$)$_q$—; R$^{10}$ represents —OH, —COOH, —CH═CH$_2$, —C(CH$_3$)═CH$_2$ or —(CH$_2$)$_r$—CH$_3$; R$^{11}$ represents —$(CH_2)_n$—$CH_3$; $n$ and $q$ lie independently in the range 1 to 15, $r$ and $s$ lie independently in the range 0 to 15; $e$ lies in the range 1 to 50, and $f$ lies in the range 1 to 300, (a³) modified polysiloxanes carrying epoxy radicals represented by formula (V):

$$CH_3-\underset{\underset{CH_3}{|}}{\overset{\overset{CH_3}{|}}{Si}}-O-\left(\underset{\underset{R^{12}}{|}}{\overset{\overset{CH_3}{|}}{Si}}-O\right)_t-\left(\underset{\underset{CH_3}{|}}{\overset{\overset{CH_3}{|}}{Si}}-O\right)_u-\underset{\underset{CH_3}{|}}{\overset{\overset{CH_3}{|}}{Si}}-CH_3 \quad (V)$$

$$O-CH_2-CH-CH_2$$
$$\diagdown O \diagup$$

in which $R^{12}$ represents —$(CH_2)_v$—; $v$ lies in the range 1 to 15; $t$ lies in the range 1 to 50, and $u$ lies in the range 1 to 300; or mixtures thereof.

Preferred modified polysiloxanes (2A) are modified polysiloxanes carrying polyethers with formula (III).

Polysiloxanes modified at the terminal portion (2B) may have formula (VI):

$$R^{13}-\underset{\underset{CH_3}{|}}{\overset{\overset{CH_3}{|}}{Si}}-O-\left(\underset{\underset{CH_3}{|}}{\overset{\overset{CH_3}{|}}{Si}}-O\right)_w-\left(\underset{\underset{CH_3}{|}}{\overset{\overset{R^{15}}{|}}{Si}}-O\right)_x-\underset{\underset{CH_3}{|}}{\overset{\overset{CH_3}{|}}{Si}}-R^{14} \quad (VI)$$

in which $R^{13}$ and $R^{14}$ may represent —OH, $R^{16}$—OH, or $R^{17}$—COOH, independently of each other; $R^{15}$ represents —$CH_3$ or —$C_6H_5$; $R^{16}$ and $R^{17}$ represent —$(CH_2)_y$—; $y$ lies in the range 1 to 15; $w$ lies in the range 1 to 200; and $x$ lies in the range 0 to 100.

Preferred polysiloxanes modified on at least one end include those carrying at least a radical ($R^{16}$ and/or $R^{17}$) carrying a carboxylic acid group on at least one terminal silicon atom.

Fluoroalkylated organosilane compounds (3) may be obtained from fluoroalkylsilanes represented by formula (VII):

$$CF_3(CF_2)_zCH_2CH_2(R^{18})_aSiX_{4-a} \quad (VII)$$

in which
$R^{18}$ represents $CH_3$—, $C_2H_5$—, $CH_3O$— or $C_2H_5O$—;
X represents $CH_3O$— or $C_2H_5O$—;
$z$ lies in the range 0 to 15 and a lies in the range 0 to 3.

In particular, the fluoroalkylsilanes may be selected from the following non limiting list: trifluoropropyltrimethoxysilane, tridecafluorooctyltrimethoxysilane, heptadecafluorodecyltrimethoxysilane, heptadecafluorodecylmethyldimethoxysilane, trifluoropropyltriethoxysilane, tridecafluorooctyltriethoxysilane, heptadecafluorodecyltriethoxysilane, heptadecafluorodecylmethyldiethoxysilane and the like, in particular trifluoropropyltrimethoxysilane, tridecafluorooctyltrimethoxysilane and heptadecafluorodecyltrimethoxysilane, and more preferably trifluoropropyl trimethoxysilane and tridecafluorooctyltrimethoxysilane.

The silane-based coupling agents may be selected from the following non limiting list: vinyltrimethoxysilane, vinyltriethoxysilane, γ-aminopropyl-triethoxysilane, γ-glycidoxypropyltrimethoxysilane, γ-mercaptopropyltrimethoxysilane, γ-methacryloxypropyltrimethoxysilane, N-β (aminoethyl)-γ-aminopropyltrimethoxysilane, γ-glycidoxypropylmethyldimethoxysilane, γ-chloropropyltrimethoxysilane, and the like.

The titanate-based coupling agents may be selected from the following list: isopropylstearoyl titanate, isopropyltris (dioctylpyrophosphate) titanate, isopropyltri(N-aminoethylaminoethyl) titanate, tetraoctylbis(ditridecylphosphate) titanate, tetra(2,2-diaryloxymethyl-1-butyl)bis(ditridecyl) phosphate titanate, bis(dioctylpyrophosphate)oxyacetate titanate, bis(dioctylpyrophosphate)ethylene titanate, and the like.

The aluminate-based coupling agents may be selected from acetoalkoxyaluminum diisopropylate, aluminum diisopropoxymonoethylacetoacetate, aluminum triethylacetoacetate, aluminum triacetylacetonate, and the like.

The zirconate-based coupling agents may be selected from the following list: zirconium tetrakisacetylacetonate, zirconium dibutoxybisacetylacetonate, zirconium tetrakisethylacetoacetate, zirconium tributoxymonoethylacetoacetate, zirconium tributoxyacetylacetonate, and the like.

The compounds acting as a binder may have a molar mass in the range 300 to 100 000.

To obtain a layer which uniformly coats the inorganic cores, the binder is preferably in the liquid state or is soluble in water or other solvents.

The quantity of binder may lie in the range 0.01% to 15%, in particular from 0.02% to 12.5%, and more particularly from 0.03% to 10% by weight (calculated with respect to C or Si) relative to the weight of particles comprising the core and the binder. Further details regarding the calculation of the relative quantity of binder can be found in patent application EP 1 184 426 A2. The relative proportion of binder may be less than or equal to 5%, e.g. less than or equal to 3%, relative to the total weight of the composite pigment.

Preparation of Composite Pigment

The composite pigment may be prepared using any appropriate method, e.g. a mechanical/chemical method or a method of precipitation in solution, with the organic coloring material being dissolved, then precipitated onto the surface of the core.

A binder may optionally be used.

A method comprising mechanically mixing an organic pigment and the inorganic core is preferred.

A binder may be added or mixed to the inorganic core before the organic coloring material is introduced.

The composite pigment may, for example, be produced using one of the processes described in European patent applications EP 1 184 426 and EP 1 217 046, the contents of which are hereby incorporated by reference, and advantageously by the process described in EP 1 184 426.

In one implementation, the particles intended to constitute the inorganic core are first mixed with the binder.

So that the binder can adhere uniformly to the surface of the inorganic core, it is preferable to pass said particles initially through a mill to disaggregate them.

The mixing and agitation conditions are selected so that the core is uniformly coated with binder. Such conditions may be controlled so that the linear load is in the range 19.6 N/cm (newtons/centimeter) to 19160 N/cm, in particular in the range 98 N/cm to 14170 N/cm and preferably in the range 147 N/cm to 980 N/cm; the treatment time is in the range 5 minutes to 24 hours, preferably in the range 10 minutes to 20 hours; the rotation rate may be in the range 2 rpm (revolutions per minute) to 1000 rpm, in particular in the range 5 rpm to 1000 rpm, and more preferably in the range 10 rpm to 800 rpm.

After coating the inorganic core with binder, the organic coloring substance is added and mixed with agitation so that it adheres to the layer of binder.

Examples of addition methods are continuous addition in large quantities, or in small quantities.

Mixing and agitation, whether of the inorganic cores with the binder or of the organic coloring substance with the inorganic cores coated with binder, may be carried out using an apparatus which can apply a sharp shearing and/or compressive force to the mixture of powders. Examples of apparatus of that type are roller mixers, blade mixers, and the like. Roller mixers are particularly suitable. A list of suitable apparatus is given in EP 1 184 426 A2.

A further method for manufacturing a composite pigment has been described in Japanese patent JP 3286463, which discloses a solution precipitation process.

The organic coloring substance is dissolved in ethanol and the inorganic cores are then dispersed in said ethanolic solution.

An aqueous alkaline solution of sodium or potassium carbonate is then slowly added to these mixtures and finally, an ethanolic calcium chloride solution is slowly added, with constant agitation.

In addition to a coloring agent absorbing light by an absorption phenomenon, the composition may include at least one interferential or diffractive pigment and/or reflective particles.

In an implementation of the invention, the first composition contains at least one goniochromatic coloring agent in which a color change can be observed as a function of the angle of observation. The goniochromatic coloring agent may optionally be magnetic.

When the first composition contains magnetic particles of a certain color and a non-magnetic goniochromatic coloring agent, said coloring agent may be selected so that its range of colors passes substantially through the color of the magnetic particles.

By way of example, this can make the magnetic particles more difficult to detect so long as they are not oriented under the effect of a magnetic field.

This can also allow the pattern induced by orienting the magnetic particles to appear only when the made-up surface is under certain observation and/or lighting conditions, thereby making it possible to create pattern disposition and appearance effects that are particularly attractive.

Reflective Particles

The composition containing the magnetic bodies may include reflective particles, in particular optionally-magnetic flakes, amongst others.

The term "reflective particles" means particles the size and structure of which, in particular the thickness of the layer or layers constituting them and their physical and chemical natures, and their surface state, allow them to reflect incident light. If appropriate, said reflection may have sufficient intensity to create highlight points on the surface of the composition or of the mixture, when the composition or the mixture is applied to the surface to be made up, which highlight points are visible to the naked eye, i.e. they are points of greater brightness that contrast with their environment and appear to shine.

The reflective particles may be selected in a manner such that they do not significantly alter the coloring effect generated by the coloring agents associated therewith, and more particularly to optimize that effect in terms of color yield. More particularly, they may have a yellow, pink, red, bronze, orangey, brown, and/or copper glint.

The reflective particles may be present in the first composition in an amount in the range 0.5% to 60% by weight relative to the total weight of the first composition, specifically 1% to 30% by weight, and in particular 3% to 10% by weight.

Said particles may be in various forms, in particular they may be in the form of flakes, or they may be globular, in particular spherical.

Regardless of their form, the reflective particles may optionally have a multilayer structure; for example, with a multilayer structure, they may have at least one layer of uniform thickness, in particular of a reflective material.

When the reflective particles do not have a multilayer structure, they may, for example, be composed of metal oxides, in particular oxides of titanium or iron obtained by synthesis.

When the reflective particles have a multilayer structure they may, for example, comprise a natural or synthetic substrate, in particular a synthetic substrate which is at least partially coated with at least one layer of a reflective material, in particular at least one metal or metallic material. The substrate may be a single material or multiple materials, and it may be organic and/or inorganic.

More particularly, it may be selected from glasses, ceramics, graphite, metal oxides, aluminas, silicas, silicates, in particular aluminosilicates and borosilicates, synthetic mica, and mixtures thereof, this list not being limiting.

The reflective material may comprise a layer of metal or of a metallic material.

Reflective particles have been described in particular in Japanese patent documents JP-A-09188830, JP-A-10158450, JP-A-10158541, JP-A-07258460 and JP-A-05017710.

Further examples of reflective particles comprising a mineral substrate coated with a metal layer that may be mentioned are particles comprising a substrate of borosilicate coated with silver.

Glass substrate particles coated with silver in the form of flakes are sold under the trade name MICROGLASS METASHINE REFSX 2025 PS by TOYAL. Glass substrate particles coated with nickel/chromium/molybdenum alloy are sold under the trade name CRYSTAL STAR GF 550, GF 2525 by the same company.

The composition containing the magnetic bodies may include at least one optionally-magnetic nacre.

OTHER COMPONENTS

Typically, the composition containing the magnetic bodies includes a physiologically acceptable medium. The term "physiologically acceptable medium" means a non-toxic medium that can be applied to the skin, to the nails, to hair, or to the lips of human beings. The physiologically acceptable medium is generally adapted to the nature of the surface onto which the composition is to be applied, and to the form in which the composition is packaged.

The composition may include ingredients other than those described above, in particular at least one solvent, one oily phase, one film-forming polymer, and/or one dermatologically or cosmetically active ingredient, in particular as a function of its dosage or "galenical" form.

Solvents

The composition containing the magnetic bodies may include at least one aqueous or organic solvent, in particular a volatile organic solvent.

The first composition may advantageously include a volatile solvent, in particular a volatile organic solvent.

The term "volatile solvent" as used in the context of the present invention means a solvent that is liquid at ambient temperature, having a non-zero vapor pressure at ambient temperature and atmospheric pressure, in particular a vapor pressure in the range 0.13 pascals (Pa) to 40000 Pa ($10^{-3}$ millimeters of mercury (mm Hg) to 300 mm Hg), and preferably in the range 1.3 Pa to 13000 Pa (0.01 mm Hg to 100 mm Hg), and preferably in the range 1.3 Pa to 1300 Pa (0.01 mm Hg to 10 mm Hg).

When the composition contains one or more organic solvents, the solvents may be present in an amount in the range 0.1% to 99%, relative to the total weight of the composition under consideration.

In general, the quantity of solvent(s), in particular organic solvent(s), depends on the nature of the surface to which the composition is intended to be applied.

The first composition may include at least one volatile solvent constituted by a volatile oil.

The oil may be a silicone oil or a hydrocarbon oil, or may include a mixture of such oils.

The term "silicone oil" as used in the context of the present invention means an oil including at least one silicon atom, and in particular at least one Si—O group.

The term "hydrocarbon oil" means an oil containing mainly hydrogen and carbon atoms and possibly oxygen, nitrogen, sulfur, and/or phosphorus atoms.

The volatile hydrocarbon oils may be selected from hydrocarbon oils having 8 to 16 carbon atoms, and in particular $C_8$-$C_{16}$ branched alkanes (also termed isoparaffins) such as isododecane (also termed 2,2,4,4,6-pentamethylheptane), isodecane, isohexadecane, and oils sold under the trade names Isopars® or Permethyls®, for example.

Volatile oils that may also be used are volatile silicones, such as volatile linear or cyclic silicone oils, for example in particular oils having a viscosity ≤8 centistokes (cSt) ($8 \times 10^{-6}$ square meters per second ($m^2$/s)), and having in particular 2 to 10 silicon atoms, and in particular 2 to 7 silicon atoms, the silicones possibly including alkyl or alkoxy groups having 1 to 10 carbon atoms. In the invention, suitable volatile silicone oils that may be mentioned are in particular dimethicones having a viscosity of 5 cSt to 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and mixtures thereof.

Mention may also be made of volatile alkyltrisiloxane linear oils of general formula (I):

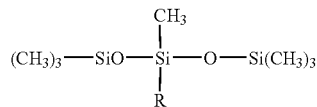

in which R represents an alkyl group comprising 2 to 4 carbon atoms and having one or more hydrogen atoms that can be substituted by a fluoride or chloride atom.

Amongst the oils of general formula (I), mention can be made of:
3-butyl 1,1,1,3,5,5,5-heptamethyltrisiloxane;
3-propyl 1,1,1,3,5,5,5-heptamethyltrisiloxane; and
3-ethyl 1,1,1,3,5,5,5-heptamethyltrisiloxane;
corresponding to oils of formula (I) for which R is respectively a butyl group, a propyl group, or an ethyl group.

It is also possible to use fluorinated volatile oils such as nonafluoromethoxybutane or perfluoromethylcyclopentane, and mixtures thereof.

A composition of the invention may contain 0.01% to 95% by weight of volatile oil relative to the total weight of the composition, for example, and preferably 1% to 75% by weight.

The composition may comprise at least one organic solvent selected from the following list:
ketones that are liquid at ambient temperature, such as methylethylketone, methylisobutylketone, diisobutylketone, isophorone, cyclohexanone, or acetone;
alcohols that are liquid at ambient temperature, such as ethanol, isopropanol, diacetone alcohol, 2-butoxyethanol, or cyclohexanol;
glycols that are liquid at ambient temperature, such as ethylene glycol, propylene glycol, pentylene glycol, or glycerol;
propylene glycol ethers that are liquid at ambient temperature, such as propylene glycol monomethyl ether, the acetate of propylene glycol monomethyl ether, or dipropylene glycol mono n-butyl ether;
short-chain esters (containing a total of 3 to 8 carbon atoms), such as ethyl acetate, methyl acetate, propyl acetate, n-butyl acetate, or isopentyl acetate; and
alkanes that are liquid at ambient temperature, such as decane, heptane, dodecane, or cyclohexane.

The composition may also comprise water or a mixture of water and hydrophilic organic solvents which are routinely used in cosmetics, such as alcohols, in particular linear or branched lower monoalcohols containing 2 to 5 carbon atoms, such as ethanol, isopropanol or n-propanol, polyols such as glycerine, diglycerine, propylene glycol, sorbitol, penthylene glycol, or polyethylene glycols. The first composition may also contain hydrophilic $C_2$ ethers and $C_2$-$C_4$ aldehydes. The water or mixture of water and hydrophilic organic solvents may be present in the first and/or second composition in an amount in the range 0% to 90%, in particular 0.1% to 90% by weight, and preferably 0% to 60% by weight, more particularly 0.1% to 60% by weight relative to the total weight of the composition.

Oily Phase

When it is to be applied to the lips or the eyelashes, the composition may, for example, include an oily phase and in particular at least one fat that is liquid at ambient temperature (25° C.) and under atmospheric pressure (760 mm of Hg) and/or a fat that is solid at ambient temperature, such as waxes, pasty fats, gums, and mixtures thereof. The oily phase may also contain lipophilic organic solvents.

By way of example, the composition may have a continuous oily phase which may contain less than 5% water, in particular less than 1% water relative to its total weight, and in particular it may be in the anhydrous form.

Fats that are liquid at ambient temperature, usually termed "oils", that may be mentioned are: hydrocarbon-containing vegetable oils such as liquid fatty acid triglycerides containing 4 to 10 carbon atoms, for example heptanoic or octanoic acid triglycerides, or sunflower, corn, soybean, grapeseed, sesame seed, apricot kernel, macadamia nut, castor, or avocado stone oil, caprylic/capric acid triglycerides, jojoba oil, shea nut butter oil, lanolin, acetylated lanolin; linear or branched hydrocarbons of mineral or synthetic origin, such as paraffin oils and their derivatives, Vaseline, polydecenes, hydrogenated polyisobutene such as Parleam; synthesized esters and ethers, in particular fatty acids such as Purcellin oil, isopropyl myristate, 2-ethylhexyl palmitate, 2-octyldodecyl stearate, 2-octyldodecyl erucate, isostearyl isostearate;

hydroxylated esters such as isostearyl lactate, octylhydroxystearate, octyldodecyl hydroxystearate, diisostearylmalate, triisocetyl citrate, fatty alcohol heptanoates, octanoates, or decanoates; isononyl isonanoate, isopropyl lanolate, tridecyl trimellilate, diisostearyl malate; polyol esters such as propylene glycol dioctanoate, neopentylglycol diheptanoate, diethyleneglycol diisononanoate; and pentaerythritol esters; fatty alcohols containing 12 to 26 carbon atoms, such as octyldodecanol, 2-butyloctanol, 2-hexyldecanol, 2-undecylpentadecanol, or oleic alcohol; hydrocarbon-containing and/or silicone-containing fluorinated oils; silicone oils such as volatile or non-volatile, linear or cyclic polymethylsiloxanes (PDMS) which may be liquid or pasty at ambient temperature, such as cyclomethicones or dimethicones, optionally comprising a phenyl group, such as phenyl trimethicones, phenyltrimethylsiloxydiphenyl siloxanes, diphenylmethyldimethyltrisiloxanes, diphenyl dimethicones, phenyl dimethicones, polymethylphenylsiloxanes; and mixtures thereof. The oils may be present in an amount in the range 0.01% to 90%, and preferably 0.1% to 85% by weight relative to the total weight of the composition.

The presence of an oily phase may impart a gloss effect, and may present a refractive index in the range 1.47 to 1.51, for example, and preferably in the range 1.48 to 1.50. The refractive index is measured at ambient temperature (25° C.) by means of a refractometer.

The composition may include at least one structuring agent for the liquid oily phase (formed by the above-described volatile or non-volatile organic solvents and/or oils) selected from waxes, semi-crystalline polymers, lipophilic gelling agents, and mixtures thereof.

Pasty fats are generally hydrocarbon-containing compounds with a melting point in the range 25° C. to 60.C, preferably in the range 30° C. to 45° C., and/or with hardness in the range 0.001 megapascals (MPa) to 0.5 MPa, preferably in the range 0.005 MPa to 0.4 MPa, such as lanolins and derivatives thereof.

Waxes may be solid at ambient temperature (25° C.) with a reversible solid/liquid change of state, with a melting point of more than 30° C. and up to 200° C., a hardness of more than 0.5 MPa, and with an anisotropic crystalline organization in the solid state. In particular, the waxes may have a melting point of more than 25° C., and preferably more than 45° C. The waxes may be hydrocarbon-containing, fluorinated and/or silicone-containing and may be of animal, mineral, vegetable and/or synthetic origin. Suitable waxes that may be mentioned are beeswax, carnauba wax or candellila wax, paraffin, microcrystalline waxes, ceresin, or ozokerite; synthetic waxes such as polyethylene or Fischer-Tropsch waxes or silicone waxes such as alkyl or alkoxydimethicone containing 16 to 45 carbon atoms. The composition may contain 0 to 50% by weight of waxes relative to the total weight of the composition, or even 1% to 30% by weight.

Suitable gums are generally high molecular weight polydimethylsiloxanes (PDMS) or cellulose gums or polysaccharides.

Film-Forming Polymers

By way of example, the composition may also include a film-forming polymer, in particular for a mascara, a nail varnish, or a foundation. The term "film-forming polymer" means a polymer that can form, by itself or in the presence of an additional film-forming agent, a continuous film that adheres to a surface, in particular to keratinous substances.

Suitable film-forming polymers for use in the composition in accordance with the invention that may be mentioned include synthetic polymers, of the radical or polycondensate type, natural polymers such as nitrocellulose or cellulose esters, and mixtures thereof.

Radical type film-forming polymers may in particular be vinyl polymers or copolymers, in particular acrylic polymers.

Vinyl film-forming polymers may result from polymerizing monomers with an ethylenically unsaturated bond containing at least one acid group and/or esters of said acid monomers and/or amides of said acid monomers, such as α,β-ethylenically unsaturated carboxylic acids, for example acrylic acid, methacrylic acid, crotonic acid, maleic acid, or itaconic acid.

Vinyl film-forming polymers may also result from homopolymerizing or copolymerizing monomers selected from vinyl esters such as vinyl acetate, vinyl neodecanoate, vinyl pivalate, vinyl benzoate, and vinyl t-butyl benzoate, and styrene monomers such as styrene and alpha-methyl styrene.

Examples of film-forming polycondensates that may be mentioned include polyurethanes, polyesters, polyester amides, polyamides, and polyureas, this list not being limiting.

Polymers of natural origin, which may optionally be modified, may be selected from shellac resin, gum sandarac, dammar resin, gum elemi, copal resin, cellulose polymers such as nitrocellulose, ethylcellulose, or nitrocellulose esters selected, for example, from cellulose acetate, cellulose acetobutyrate, and cellulose acetopropionate, and mixtures thereof.

The film-forming polymer may be present in the form of solid particles in an aqueous or oily dispersion, generally known as latexes or psuedolatexes. The film-forming polymer may comprise one or more stable dispersions of generally spherical polymer particles of one or more polymers in a physiologically acceptable liquid oily phase. Said dispersions are generally termed polymer NADs (non-aqueous dispersions), in contrast to latexes which are aqueous polymer dispersions. Said dispersions may be in the form of nanoparticles of polymers in stable dispersion in said oily phase. The nanoparticle size is preferably in the range 5 nm to 600 nm. Techniques for preparing said dispersions are well known to the person skilled in the art.

Aqueous film-forming polymer dispersions which may be used are acrylic dispersions sold under the trade names NEOCRYL XK-90®, NEOCRYL A-1070®, NEOCRYL A-1090®, NEOCRYL BT-62®, NEOCRYL A-1079®, NEOCRYL A-523® by AVECIA-NEORESINS, and DOW LATEX 432® by DOW CHEMICAL; DAITOSOL 5000 AD® by DAITO KASEI KOGYO; or aqueous polyurethane dispersions sold under the trade names NEOREZ R-981® and NEOREZ R-974® by AVECIA-NEORESINS; AVALURE UR-405®, AVALURE UR-410®, AVALURE UR-425®, AVALURE UR-450®, SANCURE 875®, SANCURE 861®, SANCURE 878®, and SANCURE 2060® by GOODRICH; IMPRANIL 85® by BAYER; AQUAMERE H-1511® by HYDROMER; and sulfopolyesters sold under the trade mark Eastman AQ by Eastman Chemical Products.

Sequenced Film-Forming Polymer

In an embodiment of the invention, the composition includes at least one film-forming polymer that is a film-forming linear sequenced ethylene polymer. The polymer preferably comprises at least a first sequence and at least a second sequence having different glass transition temperatures (Tg), said first and second sequences being connected together by an intermediate sequence comprising at least one monomer that constitutes the first sequence and at least one monomer that constitutes the second sequence.

The first and second sequences of the sequenced polymer are advantageously incompatible with each other.

By way of example, such polymers are described in documents EP 1 411 069 or WO04/028488 which are incorporated herein by reference.

The composition containing the magnetic bodies may contain at least one optionally-magnetic filler.

Fillers

The term "filler" means particles of any form which are insoluble in the composition medium regardless of the temperature at which the composition is manufactured. A filler primarily acts to modify the rheology or texture of the composition. The nature and quantity of the particles could depend on the desired mechanical properties and textures.

Examples of fillers that may be mentioned include amongst others talc, mica, silica, kaolin, and sericite, and powders of polyamide, polyolefin, e.g. polyethylene, polytetrafluoroethylene, polymethylmethacrylate, or polyurethane, powdered starch, and silicone resin beads.

Amongst other things, the fillers may be intended to create a fuzzy effect, in particular for a foundation, so as to conceal skin imperfections.

The composition containing the magnetic bodies may also include a film-forming auxiliary agent that encourages the formation of a film with the film-forming polymer.

Active Ingredients

The composition may include at least one cosmetically or dermatologically active ingredient. Suitable cosmetically, dermatologically, hygienically, or pharmaceutically active ingredients for use in the compositions of the invention that may be mentioned are moisturizing agents (polyols such as glycerine), vitamins (C, A, E, F, B, or PP), essential fatty acids, essential oils, ceramides, sphingolipids, liposoluble or nanoparticle sun screens, and specific skin treatment active ingredients (protective agents, antibacterials, anti-wrinkle agents, etc), self-tanning agents. Said active ingredients may be used in concentrations in the range 0 to 20%, for example, in particular in the range 0.001% to 15% relative to the total weight of the composition.

The composition may also contain ingredients that are routinely used in cosmetics, such as thickeners, surfactants, oligo-elements, moisturizing agents, softeners, sequestrating agents, fragrances, alkalinizing or acidifying agents, preservatives, antioxidants, UV filters, colorants, or mixtures thereof.

Depending on the envisaged application, the composition of the invention may include constituents which are conventionally used in the fields under consideration, and which are present in quantities appropriate to the desired dosage form.

Dosage Forms

The composition may be in a variety of forms, depending on its purpose. The composition may thus be in any dosage form that is normally used for topical application, in particular in the anhydrous form, in the form of an oily or aqueous solution, an oily or aqueous gel, an oil-in-water or a water-in-oil emulsion, a wax-in-water or a water-in-wax emulsion, a multiple emulsion or a dispersion of oil in water due to vesicles located on the oil/water interface.

The composition may be in the form of a powder, or even a gel.

MAGNETIC DEVICES

The magnetic device may comprise a permanent magnet or an electromagnet powered by at least one optionally-rechargeable battery, for example. For a battery, the magnetic device may include a switch enabling the electromagnet to be powered selectively with electricity.

The magnetic device may be arranged so as to create a magnetic field of orientation that varies over time. When the magnetic device comprises a magnet, the device may, for example, include a motor enabling the magnet to be rotated. In a variant, the magnetic device may comprise a plurality of solenoids disposed so as to generate a rotating magnetic field when powered sequentially with electricity.

By way of example, a rotating magnetic field may make it possible to obtain a pattern presenting circular symmetry, e.g. a pattern giving the impression of a sphere in relief.

The electromagnet(s) may be powered continuously or intermittently, as desired by the user. In particular, the magnetic device may be arranged so that the electromagnets(s) need not be powered while the magnetic device is not correctly positioned close to the surface coated with the first composition.

The magnetic field is at least 50 milli teslas (mT), for example, even at least 66 mT, better at least 0.2 T, or even at least 1 T (10000 Gauss).

In order to make it easier to apply the magnetic field, the magnetic device may include a member enabling it to be positioned relative to the surface on which the composition has been deposited. This makes it possible to prevent the magnetic device from accidentally coming into contact with the composition and/or makes it possible to center the pattern formed on the region under consideration.

In an implementation of the invention, the magnetic device is secured to an applicator that is used to apply the cosmetic composition. This makes it possible to reduce the number of objects that need to be manipulated by the user and makes it easier to apply makeup.

In another implementation of the invention, the magnetic device comprises a magnet mounted at a first end of a rod having a second end that is connected to a handle of an applicator that is used to apply the cosmetic composition.

The magnetic field may also be exerted by means of a magnetic structure, in particular a flexible structure, including alternate N and S poles. By way of example, such a structure may make it possible to form repeated patterns, e.g. stripes, on the first composition.

KITS FOR IMPLEMENTING THE METHOD

In another of its aspects, the invention also provides, a kit for implementing the method as defined above, said kit comprising:
  a magnetic device enabling a magnetic field to be generated; and
  a cosmetic composition including:
    magnetic bodies that present non-zero magnetic susceptibility and that are movable under the effect of a magnetic field; and
    at least one diffractive pigment; the magnetic device being capable of creating a magnetic field that is capable, when the keratinous substance covered in a deposit of said composition is inserted in said magnetic field, of modifying the orientation and/or the position of the magnetic bodies inside the deposit.

In particular, the magnetic device may be arranged so as to generate a magnetic field that is sufficiently strong to be able to modify the orientation and/or the position of the magnetic bodies within the composition after it has been applied to a surface such as the skin, the lips, the nails, or hair, in order to change their appearance.

By way of example, when the first composition contains a volatile solvent, the magnetic field is exerted shortly after it has been deposited, so as to change the appearance of said composition before it has dried.

By way of example, the composition may be a nail varnish, a foundation, or a lipstick, and may present the characteristics as defined above.

The magnetic device may be as defined above.

The kit may comprise a compact housing the first cosmetic composition and the magnetic device. In this event, the compact may, for example, include a plurality of magnets of various shapes in order to produce different patterns.

The kit may also include an additional cosmetic composition for applying to the above-mentioned composition, or to the surface before the above-mentioned composition is applied.

The invention can be better understood on reading the following detailed description of non-limiting implementations thereof, and on examining the accompanying drawings, in which.

Figure 16:
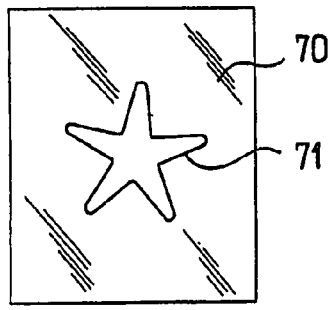
Figure 17:
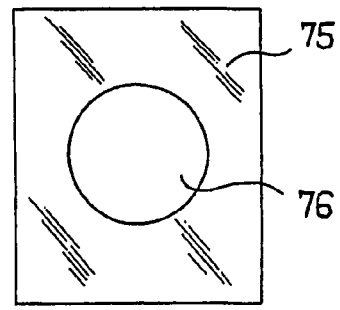

FIG. 16 shows a perforated mask that is suitable for being used during implementation of the method of the invention; and FIG. 17 shows a magnetic sheet that is suitable for being used during implementation of the method of the invention; and In the figures, magnetic bodies are shown in the form of dots in order to make the drawings easy to understand, but in reality the individual bodies need not be visible to the naked eye.

Figure 1:
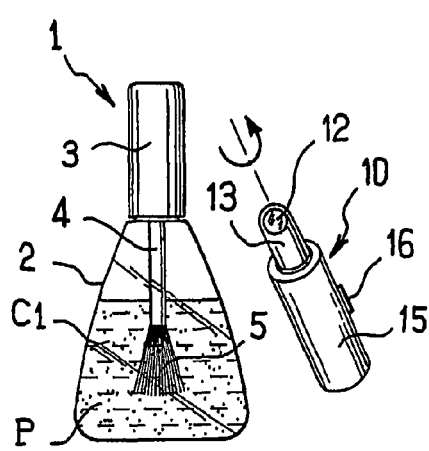
FIG. 1 is a diagram showing an example of a kit of the invention.
Figure 2:
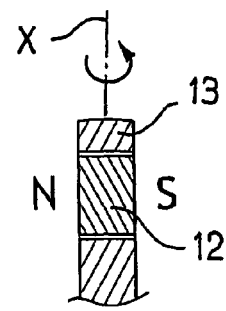
FIG. 2 is a diagrammatic and fragmentary axial section view showing the magnetic device of FIG. 1.

FIG. 1 shows a kit 1 comprising a cosmetic composition $C_1$ containing magnetic particles P having orientation and/or position that affects the appearance of the composition after it has been deposited on a surface such as the skin, the lips, the nails, hair, or even false nails.

In the embodiment shown, the composition $C_1$ is a nail varnish contained in a receptacle 2 that is closed by a cap 3. The cap supports a non-magnetic cosmetics applicator 4 including an applicator member 5 constituted by a brush enabling the varnish to be applied to the nails.

The kit 1 further comprises a magnetic device 10 that makes it possible to generate a magnetic field that is useful for changing the appearance of the composition $C_1$ without making contact therewith.

In the embodiment under consideration, the magnetic device 10 comprises a permanent magnet 12 supported by a support member 13 of longitudinal axis X, the polar axis of the magnet 12 being substantially perpendicular to the axis X.

In the embodiment under consideration, the magnetic device 10 is arranged to generate a rotating magnetic field, and includes a motor (not shown), housed in a casing 15, so as to rotate the support member 13 about it axis X.

A switch 16 is present on the casing 15 so as to enable the user to switch on the motor, thereby rotating the support member 13 together with the magnet 12.

In a variant not shown, the rotating magnetic field is generated by a plurality of solenoids that are powered sequentially so as to generate a rotating field.

Figure 3:
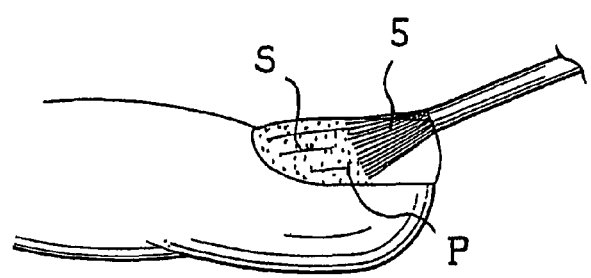
FIGS. 3 and 4 are diagrams showing the kit being used.

In order to use the kit 1, the user can begin, as shown in FIG. 3, by applying the composition $C_1$ by means of an applicator 4 to the surface S to be made up, specifically a fingernail.

Figure 4:
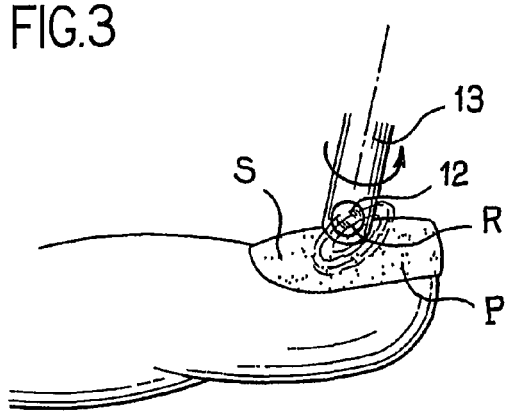

In the subsequent step shown in FIG. 4, the user brings the magnetic device 10 over a central region R of the surface S and actuates the switch 16 so as to make the magnet 12 turn.

The magnetic particles contained in the composition $C_1$ tend to come into alignment with the field lines of the magnet 12 and change orientation, thereby leading to a change in the appearance of the composition $C_1$.

The user can choose the length of time the magnetic field is to be applied as a function of the desired result.

Figure 5:
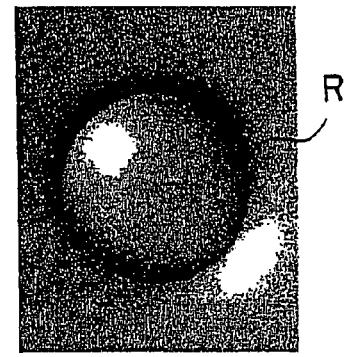
FIG. 5 shows an example of a pattern that can be obtained by means of the invention.

By way of example, the pattern obtained can give the impression of a sphere in relief, as shown in FIG. 5.

Figure 6:
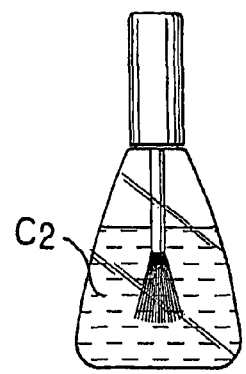
FIG. 6 is a diagram showing a receptacle containing an additional composition that is suitable for being applied to the surface.

If necessary, the user can apply a second composition $C_2$, e.g. a transparent varnish, contained in a receptacle shown in FIG. 6, once the composition $C_1$ has dried.

Applying the second composition $C_2$ makes it possible to create an effect of additional depth, for example.

In the nail varnish embodiment in FIGS. 1 to 5, the composition $C_1$ may have the following formulation, with quantities being expressed in percentages by weight in all of the examples below.

EXAMPLE A

| | |
|---|---|
| Nitrocellulose | 11 |
| N-ethyl o,p-toluenesulfonamide | 5 |
| Alkyde resin | 10 |
| Isopropanol | 4 |
| Interferential magnetic pigment* | 0.5 |
| Butyl acetate/ethyl acetate 50/50 | Qsp 100 |

*Nacres containing at least 14% of $Fe_3O_4$, referenced COLORONA PATINA GOLD (117288), and sold by MERCK.

The appearance of such a nail varnish can be changed by applying a magnetic field before the varnish has had time to dry.

By way of example, when a second composition $C_2$ is applied to the first, said second composition has the following formulation.

EXAMPLE B

| Nitrocellulose | 11 |
|---|---|
| N-ethyl o,p-toluenesulfonamide | 5 |
| Alkyde resin | 10 |
| Isopropanol | 4 |
| Butyl acetate/ethyl acetate 50/50 | Qsp 100 |

Such a composition makes it possible to create an effect of additional depth.

In a variant, the second composition may be intended to create a colored base, and it is applied before the first. By way of example, the second composition then has the following formulation.

EXAMPLE C

| Nitrocellulose | 11 |
|---|---|
| N-ethyl o,p-toluenesulfonamide | 5 |
| Alkyde resin | 10 |
| Isopropanol | 4 |
| DC RED7 CI 15850 pigment | 2 |
| Magnetic pigment* | 0.2 |
| Interferential pigment** | 3 |
| Butyl acetate/ethyl acetate 50/50 | Qsp 100 |

*STAPA WM IRON VP 041040 by ECKART.
**Xirona Kiwi-Rose by Merck.

When it is subjected to a magnetic induction field, the composition presents a decorative appearance that is frozen after drying. The addition of the interferential pigment makes it possible to impart an additional color effect overall so as to enhance the effect provided by the particle having magnetic susceptibility. In the example under consideration, a goniochromatic effect is used between the colors green and pink.

Figures 7, 8, 9:
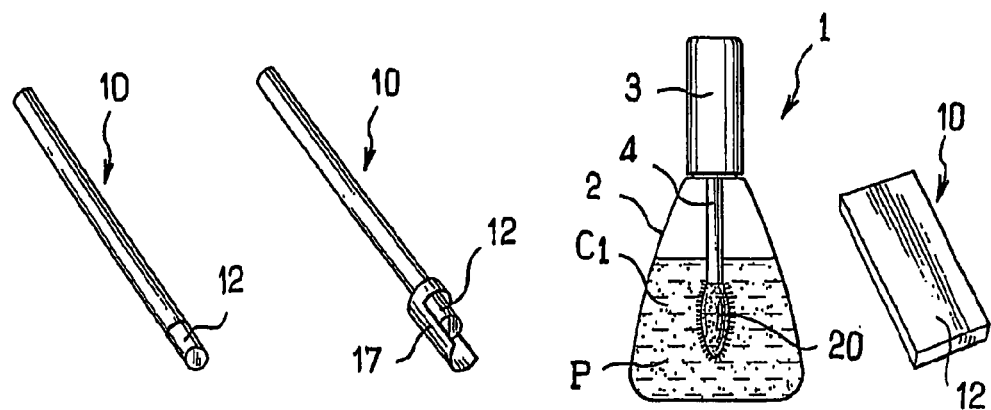
FIG. 7 is a diagram showing, in isolation, another example of a magnetic device that can be used.
FIG. 8 is a diagram showing the FIG. 7 magnetic device provided with a positioning member for positioning the magnet facing the made-up surface.
FIGS. 9 and 10 are diagrams of other examples of kits of the invention.

Naturally, whatever the nature of said composition, the magnetic field applied thereto need not rotate. By way of example, FIG. 7 shows a magnetic device which, at its end, includes a permanent magnet 12 in the form of a bar.

When the magnetic field does not rotate, the user can, for example, move the magnet into the vicinity of the composition $C_1$ as a function of the desired result.

Whatever its nature, the magnetic device may include a member enabling it to be positioned relative to the surface S.

By way of example, the positioning member serves to prevent the magnetic device from touching the composition while the magnetic field is being exerted.

The positioning member can also serve to center the pattern that is produced relative to the surface S, e.g. the nail.

Depending on the nature of the surface, the positioning member could take various forms, e.g. that of an extension 17 offering an abutment surface for engaging the end of the finger, as shown in FIG. 8.

FIG. 9 shows another embodiment of a kit 1 of the invention, including a first composition $C_1$ constituted in this embodiment by a liquid lipstick or a lipgloss.

In this embodiment, the applicator 4 comprises a flocked endpiece 20 supported by the cap 3 of the receptacle 2.

By way of example, the magnetic device 10 is in the form of a flexible structure, e.g. made of plastics material filled with magnetized particles, creating alternate N and S poles, thereby making it possible to form repeated patterns, e.g. stripes, on the surface coated with the first composition.

By way of example, for lipstick, the composition $C_1$ presents the following formulation.

EXAMPLE D

| Octyl-2 dodecanol | 10 |
|---|---|
| Ditertiobutyl 4-hydroxytoluene | 0.07 |
| Polybutene (monoolefins/isoparaffins 95/5) (PM: 2060) | 50 |
| A mixture of isopropyl, isobutyl, and n-butyl p-hydroxybenzoates (40/30/30) | 0.4 |
| Pentaerythrityl tetraisostearate | 11.33 |
| Tridecyle trimellitate | 13 |
| 2-décyl tetradecanoic acid triglyceride (GUERBET C24) | 15 |
| Interferential magnetic pigment* | 0.2 |

*Nacres containing at least 14% of $Fe_3O_4$, sold under the reference CLOISONNE NU ANTIQUE GREEN 828 CB by ENGELHARD.

Figures 10, 11, 12:
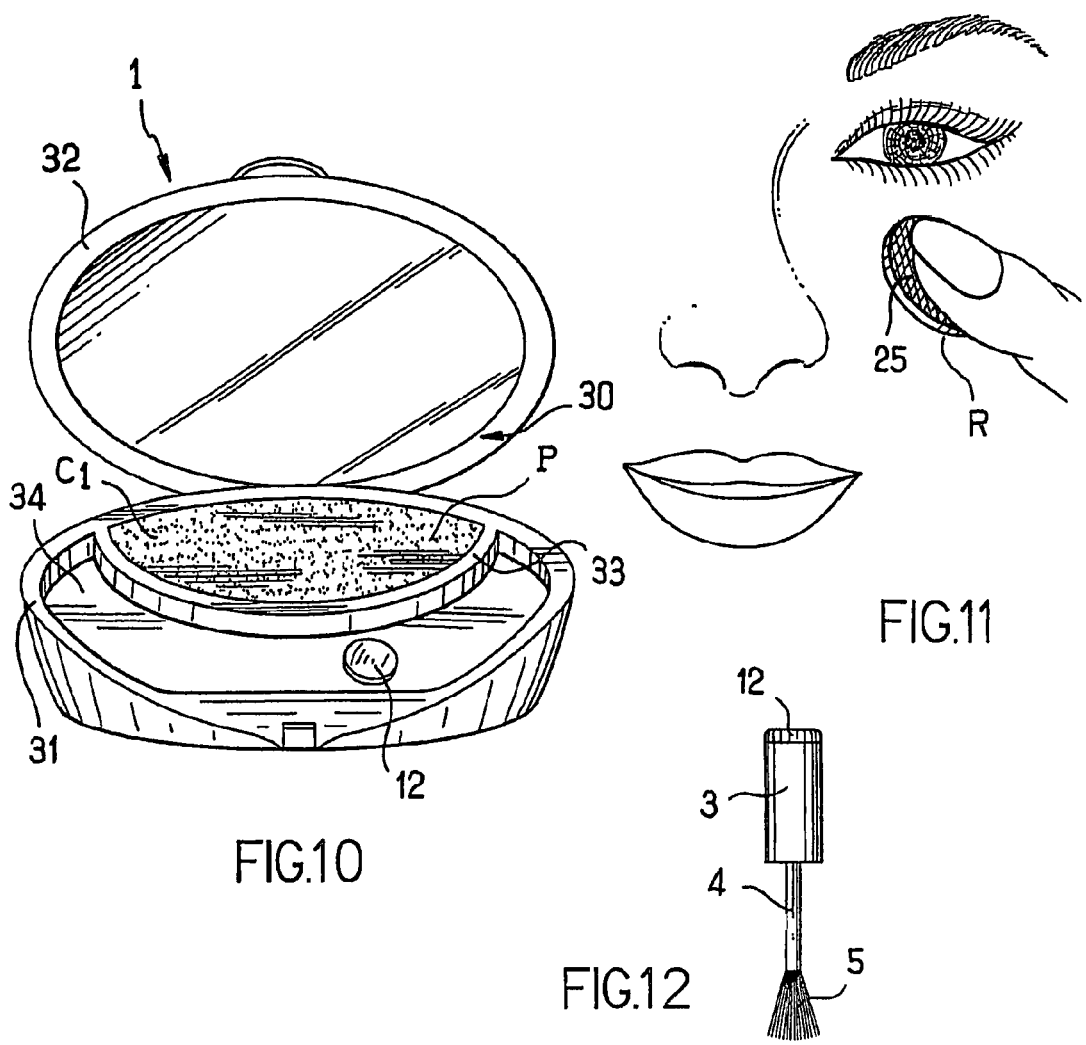
FIG. 11 shows the FIG. 10 kit being used.
FIG. 12 is a diagram showing, in elevation and in isolation, an example of an applicator secured to a magnetic device.

Another kit 1 of the invention is shown in FIG. 10. In this embodiment, the kit 1 includes a compact 30 constituted by a base body 31 and a lid 32 hinged thereon.

The base body 31 includes a compartment 33 housing the composition $C_1$, which, in the embodiment shown, is constituted by a foundation in the form of a paste.

The base body 31 includes a housing 34 arranged to receive at least one magnet 12.

By way of example, the magnet 12 may present an adhesive face 25 or any other mounting means enabling the user to fix it to the end of a finger so as to bring it into the vicinity of the made-up zone, e.g. a region of the face as shown in FIG. 11.

After applying the composition $C_1$ to the skin, the user can modify the clarity of said composition by exposing it to the magnetic field generated by the magnet 12.

By way of example, for a composition for making up the skin, said composition can have the following formulation.

EXAMPLE E

| Magnesium sulfate | 1.5 |
|---|---|
| Sodium carboxymethylcellulose | 0.5 |
| Distearyldimethylammonium modified hectorite | 1 |
| Cyclopenta dimethylsiloxane | 16 |
| Glycerol | 5 |
| A mixture of oxyethylenated polymethylketyldimethyl methylsiloxane, polyglycerol isostearate (4 moles), hexyl laurate | 9 |
| Water | 31.6 |
| A mixture of ethylene glycol acetyl stearate, glyceryl tristearate | 0.3 |
| Brown iron oxide coated with aluminum stearoyl glutamate (97/3) | 1.58 |
| Anatase titanium oxide coated with stearoyl glutamate (97/3) | 18.17 |
| Yellow iron oxide coated with aluminum stearoyl glutamate (93/3) | 4.56 |
| Black iron oxide coated with aluminum stearoyl glutamate (97/3) | 0.69 |
| Polydimethylsiloxane (viscosity: 5 cSt) | 6 |
| Interferential magnetic pigment* | 0.5 |
| 1,2-pentanediol | 3 |

*Nacres with at least 14% of $Fe_3O_4$, sold by Merck under the reference TIMICA NU ANTIQUE BRONZE 240 AB.

Whatever the type of applicator, the magnet 12 may, where appropriate, be incorporated in the applicator.

In the embodiment in FIG. 12, the closure cap 3 is surmounted by the magnet 12 on the side remote from the applicator member 5.

Figure 13:
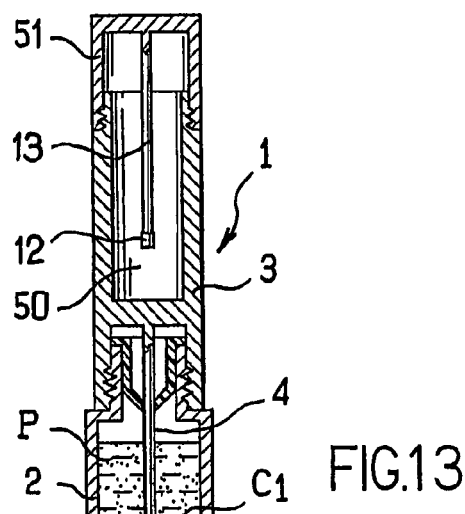
FIG. 13 is an axial and diagrammatic section of another example of a kit of the invention.

In the embodiment in FIG. 13, the magnet 12 is supported by a support member 13 surmounted by a cap 51, and can, when not in use, be housed in a compartment 50 of the cap 3 for closing the receptacle 2 containing the first composition $C_1$. The cap 51 serves as a handle for the magnet 12, and also serves to close the compartment 50.

It is not beyond the ambit of the present invention for the magnetic field to be generated by an electromagnet instead of by a permanent magnet.

Figure 14:
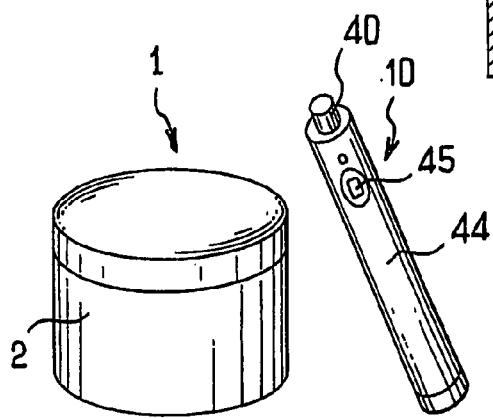
FIG. 14 is a diagram showing another example of a kit of the invention.

FIG. 14 shows a kit 1 comprising a receptacle 2 constituted by a pot containing the first composition $C_1$, and a magnetic device 10 comprising an electromagnet 40 at one end of a casing 44 housing the power supply.

A switch 45 enables the electromagnet 40 to be switched on selectively by the user.

Various devices other than those described above for packaging and/or dispensing or applying the composition $C_1$ can be used.

Figure 15:
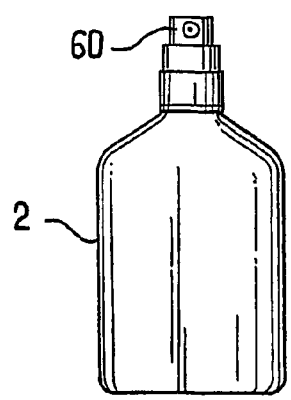
FIG. 15 shows another example of a packaging device for the composition.

By way of example, the composition $C_1$ can be deposited on the surface S without using an applicator, but in the form of a spray, e.g. by using a pump 60 as shown in FIG. 15. The spray can also be generated by means of an airbrush or by a pressurized receptacle, for example.

A perforated mask 70, as shown in FIG. 16 in which its perforation pattern 71 is in the shape of a star, can be interposed between the spray and the surface to be made up.

An optionally-perforated sheet 75 that is permeable to the magnetic field can be interposed between the magnet 12 or the electromagnet 40 and the surface S, so as to change the shape of the field lines and create novel effects.

Naturally, the invention is not limited to the examples given above.

For example, the kit may include a plurality of magnets having various shapes, so as to create various patterns.

The expression "comprising a" should be understood as being synonymous with "comprising at least one", and the expression "in the range" should be understood as including the limits of the range.

The invention claimed is:

1. A method of applying nail varnish to nails, comprising:
    manually depositing, using a non-magnetic cosmetic applicator, at least nail varnish on a surface of a human nail, the nail varnish comprising:
        magnetic bodies that are movable under the effect of a magnetic field; and
        at least one interferential pigment; and
    after the depositing, manually exposing at least part of nail varnish to a magnetic device producing a magnetic field, the magnetic device located above the nail varnish during the exposing, so as to modify the orientation and/or displace at least some of the magnetic bodies resulting in formation of a visible pattern on the nail varnish according to the magnetic field of the magnetic device, the magnetic bodies within the pattern being oriented and/or displaced differently than the magnetic bodies outside of the pattern.

2. The method according to claim 1, in which the magnetic field is exerted by a permanent magnet.

3. The method according to claim 1, in which the magnetic field is exerted by an electromagnet.

4. The method according to claim 2, in which the magnet or electromagnet is rotated.

5. The method according to claim 3, in which the electromagnet is powered by at least one battery.

6. The method according to claim 3, in which the electromagnet is switched on intermittently while the pattern is being formed.

7. The method according to claim 1, in which the magnetic field is applied until the nail varnish obtains a fixed appearance.

8. The method according to claim 1, in which the magnetic field is applied for a period of time that is shorter than the period of time that causes all of the magnetic bodies in the exposed region to be permanently displaced and/or oriented.

9. The method according to claim 1, in which the magnetic field is exerted successively on different regions of the surface that are coated with the nail varnish.

10. The method according to claim 9, wherein the magnetic field is exerted successively on regions of the surface that are disjoint.

11. The method according to claim 1, in which at least one region of the surface that is coated with the nail varnish is not exposed to the magnetic field.

12. The method according to claim 1, in which the applicator comprises a brush, a flocked endpiece, or a foam.

13. The method according to claim 1, wherein the magnetic bodies particles are made up, at least in part, of the interferential pigment.

14. The method according to claim 1, in which the magnetic bodies are different from the particles of the interferential pigment.

15. The method according to claim 1, wherein the magnetic bodies comprise fibers or particle chains.

16. The method according to claim 1, in which the interferential pigment is a goniochromatic pigment.

17. The method according to claim 1, in which the interferential pigment comprises reflective particles.

18. The method according to claim 1, in which the nail varnish includes at least one volatile solvent.

19. The method according to claim 1, in which the nail varnish includes at least one film-forming polymer.

20. A method of applying makeup to a nail, comprising:
    manually depositing, using a non-magnetic cosmetic applicator at least one cosmetic composition on a surface of the nail, the cosmetic composition comprising:
        magnetic bodies that are movable under the effect of a magnetic field;
        and at least one interferential pigment;
    and after the depositing, manually engaging a portion of a magnetic device with a portion of the nail such that neither a magnet of the magnetic device nor the engaged portion of the magnetic device contacts the surface or the composition;
    exposing at least part of the composition to a magnetic field of the magnet, the magnetic device located above the cosmetic composition during the exposing, so as to modify the orientation and/or displace at least some of the magnetic bodies resulting in formation of at least one visible pattern on the composition according to the magnetic field of the magnetic device, the magnetic bodies within the pattern being oriented and/or displaced differently than the magnetic bodies outside of the pattern.

21. The method of claim 20, wherein the portion of the magnetic device is a positioning member.

22. The method of claim 21, wherein the positioning member is an abutment surface.

23. The method of claim 1, wherein the pattern is recognizable as at least one of a star, a sphere in relief, and stripes.

24. The method of claim 20, wherein the pattern is recognizable as at least one of a star, a sphere in relief, and stripes.

25. The method of claim 1, wherein the pattern is a repeated pattern.

26. The method of claim 20, wherein the pattern is a repeated pattern.

* * * * *